US011753655B2

(12) United States Patent
Bailey et al.

(10) Patent No.: US 11,753,655 B2
(45) Date of Patent: Sep. 12, 2023

(54) COMPOSITIONS AND METHODS FOR TREATMENT OF NEUROLOGICAL DISORDERS

(71) Applicant: THE BOARD OF REGENTS OF THE UNIVERSITY OF TEXAS SYSTEM, Austin, TX (US)

(72) Inventors: Rachel M. Bailey, Trophy Club, TX (US); Steven J. Gray, Southlake, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 219 days.

(21) Appl. No.: 17/230,484

(22) Filed: Apr. 14, 2021

(65) Prior Publication Data

US 2021/0324411 A1    Oct. 21, 2021

Related U.S. Application Data

(60) Provisional application No. 63/010,179, filed on Apr. 15, 2020.

(51) Int. Cl.
| | |
|---|---|
| *C12N 15/86* | (2006.01) |
| *C07K 14/01* | (2006.01) |
| *A61P 25/02* | (2006.01) |
| *A61K 48/00* | (2006.01) |
| *C07K 16/08* | (2006.01) |

(52) U.S. Cl.
CPC ............ *C12N 15/86* (2013.01); *A61K 48/005* (2013.01); *A61P 25/02* (2018.01); *C07K 14/01* (2013.01); *C07K 16/081* (2013.01)

(58) Field of Classification Search
CPC ....... C12N 15/86; A61P 25/02; A61K 48/005; C07K 14/01; C07K 16/081
See application file for complete search history.

(56) References Cited

U.S. PATENT DOCUMENTS

| | | | | |
|---|---|---|---|---|
| 2007/0292922 A1* | 12/2007 | Fang | .................... | C07K 14/005 |
| | | | | 435/69.6 |
| 2014/0213842 A1* | 7/2014 | Simon | ................ | A61N 1/36075 |
| | | | | 607/46 |
| 2014/0336128 A1* | 11/2014 | Payne | .................... | C07K 14/47 |
| | | | | 435/375 |
| 2016/0331846 A1* | 11/2016 | Keimel | ................ | C12N 9/2402 |
| 2018/0193414 A1* | 7/2018 | Greenberg | .............. | A61P 25/16 |
| 2019/0269800 A1 | 9/2019 | Ferreira | | |

OTHER PUBLICATIONS

Taghian, Toloo, et al. "A safe and reliable technique for CNS delivery of AAV vectors in the cisterna magna." Molecular Therapy 28.2 (2020): 411-421. (Year: 2020).*
Taghian et al., "A Safe and Reliable Technique for CNS Delivery of AAV Vectors in the Cisterna Magna", Molecular Therapy, vol. 28, No. 2, pp. 411-421.
PCT International Application No. PCT/US2021/027266, Written Opinion of The International Searching Authority, dated Sep. 17, 2021, 8 pages.
PCT International Application No. PCT/US2021/027266, International Search Report of The International Searching Authority, dated Sep. 17, 2021, 4 pages.

* cited by examiner

*Primary Examiner* — Nancy J Leith
*Assistant Examiner* — Khaleda B Hasan
(74) *Attorney, Agent, or Firm* — DLA Piper LLP, US

(57) ABSTRACT

The present disclosure provides methods and compositions for the treatment of diseases and/or disorders in a subject, including, but not limited to neurological disorders such as giant axonal neuropathy. The methods described herein include direct administration of a gene therapy (e.g. an rAAV viral vector) to a subject via injection into a vagus nerve (e.g. the left vagus nerve) of the subject.

18 Claims, 4 Drawing Sheets

Specification includes a Sequence Listing.

COMPOSITIONS AND METHODS FOR TREATMENT OF NEUROLOGICAL DISORDERS

CROSS REFERENCE TO RELATED APPLICATIONS

This application claims priority to U.S. Provisional Application No. 63/010,179, filed Apr. 15, 2020, the contents of which are incorporated by reference herein in their entirety for all purposes.

GOVERNMENT SUPPORT

This invention was made with government support under grant NS087175 awarded by the National Institutes of Health. The government has certain rights in the invention.

INCORPORATION BY REFERENCE OF SEQUENCE LISTING

The instant application contains a Sequence Listing which has been submitted in ASCII format via EFS-Web and is hereby incorporated by reference in its entirety. Said ASCII copy, created on Apr. 14, 2021 is named "TAYS-010_SeqList.txt" and is about 28,912 bytes in size.

BACKGROUND

Adeno-associated virus (AAV)-based gene therapies are becoming increasingly prevalent in the treatment of a wide variety of different diseases, including the treatment of neurological disorders and their associated autonomic dysfunctions. However, recent research has shown that neutralizing antibodies against certain AAV serotypes are highly prevalent in the human population. In fact, some studies have indicated that the prevalence of neutralizing antibodies against AAV1, AAV2, AAV5, AAV6, AAV8 and AAV9 could be as high as 70%, 70%, 40%, 46%, 38% and 47%, respectively. In individuals that are positive for neutralizing antibodies, AAV-based gene therapy may be infeasible. Finally, the presence of neutralizing antibodies is particularly problematic in the context of subjects who have previously been administered a first AAV-based gene therapy and that are in need of: a) an additional dose of the first AAV-based gene therapy; or b) a different AAV-based gene therapy. Accordingly, there is a need in the art for compositions and methods for the administration of AAV-based gene therapies that overcome the problems associated with the presence of neutralizing antibodies in a subject. Additionally, there is a need in the art for compositions and methods directed to the delivery of gene therapy vectors to the autonomic nervous system of a subject, including subjects who are seropositive for gene therapy vectors like AAV.

Giant Axonal Neuropathy is a rare, devastating neurological disorder that begins in early childhood at 3 to 4 years of age, generally manifesting with sensory ataxia. In the peripheral nervous system (PNS), the disease progressively affects sensory and motor nerves. Pathology is also apparent throughout the autonomic nervous system (ANS) and patients frequently present with enteric and autonomic dysfunction in the form of dysarthria, dysphagia, issues with GI motility, and respiratory, difficulties. Patients typically become wheelchair dependent with limited use of the arms and little to no use of their legs by the end of the second decade of life. Moreover, during the second decade of life, a tracheostomy (or other means of ventilation), as well as a feeding tube, are often necessary. Giant Axonal Neuropathy also affects the central nervous system, as MRI results from patients with Giant Axonal Neuropathy often show white matter abnormalities in the brain and cerebellum and eventually severe atrophy of the brainstem and spinal cord in later stages of the disease. Death typically occurs by the third decade of life. Giant axonal neuropathy is an autosomal recessive genetic disorder caused by an abnormality in the GAN gene located on chromosome 16 at 16q24.1 that codes for the gigaxonin (GAN) protein. The abnormal GAN protein causes a portion of the nerve cell called the axon to swell up with deposits of tiny threads of protein called neural aments, giving the appearance of giant axons. The giant axons cause degeneration and abnormal functioning of the peripheral nervous system. There is no current treatment for Giant Axonal Neuropathy. Thus, there is a need in the art for compositions and methods directed to the treatment of Giant Axonal Neuropathy.

SUMMARY

The present disclosure relates generally to the field of gene therapy, including, but not limited to, recombinant adeno-associated virus (rAAV)-based gene therapy. More specifically, the present disclosure relates generally to the administration of rAAV viral vectors to subjects who have been previously administered an rAAV-based gene therapy and/or are seropositive for neutralizing antibodies against one or more AAV serotypes. The present disclosure provides compositions and methods for the administration of at least one rAAV viral vector to a subject via injection into at least one vagus nerve of the subject. The present disclosure also provides rAAV viral vectors comprising transgene sequences encoding for gigaxonin (GAN) polypeptides, their manufacture, and their use to deliver transgenes to treat or prevent a disease or disorder, including diseases associated with loss, misfunction and/or deficiency of the GAN gene.

The present disclosure provides a method of treating a disease and/or disorder in a subject comprising administering to the subject at least one therapeutically effective amount of a recombinant adeno-associated virus (rAAV) viral vector by injecting the at least one therapeutically effective amount of the rAAV viral vector into a vagus nerve of the subject.

In some aspects, a vagus nerve can be the left vagus nerve of the subject.

In some aspects, a disease and/or disorder can be a neurological disease and/or disorder.

In some aspects, a neurological disease and/or disorder is characterized by at least one autonomic dysfunction, and wherein administration of the at least one therapeutically effective amount of the rAAV viral vector via injection into the vagus nerve alleviates at least one symptom of the at least one autonomic dysfunction. In some aspects, an at least one symptom can be selected from dysarthria, dysphagia, inadequate control of gastrointestinal tract motility, inadequate control of blood pressure, respiratory difficulties, orthostatic hypotension, sweating abnormalities, inadequate control of urinary tract, sexual dysfunction, and any combination thereof.

In some aspects, a disease and/or disorder can be selected from Spinal muscular atrophy, Friedrich's ataxia, CLN3 Batten, CLN6 Batten, CLN7 Batten, Epileptic encephalopathy, Leigh Syndrome, Charcot Marie Tooth disease, Giant axonal neuropathy, Lafora disease, SLC13A5 Epileptic Encephalopathy, Congenital Disorder of Glycosylation, Type Iq, Kahrizi Syndrome, Angelman Syndrome, Rett Syndrome, Spastic paraplegia, Alternating hemiplegia of childhood and Zellweger spectrum disorder. In some aspects, a disease and/or disorder can be Giant Axonal Neuropathy.

In some aspects, an rAAV viral vector can comprises: (i) an AAV capsid protein; and (ii) an rAAV vector, wherein the rAAV vector comprises in the 5' to 3' direction: a) a first AAV ITR sequence; b) a promoter sequence; c) a transgene nucleic acid molecule, wherein the transgene nucleic acid molecule comprises a nucleic acid sequence encoding for a gigaxonin (GAN) polypeptide; d) a polyA sequence; and e) a second AAV ITR sequence.

In some aspects, a GAN polypeptide can comprise the amino acid sequence set forth in SEQ ID NO: 1.

In some aspects, a nucleic acid sequence encoding for a GAN polypeptide can be a codon optimized nucleic acid sequence encoding for a GAN polypeptide, wherein the codon optimized nucleic acid sequence encoding for a GAN polypeptide comprises the nucleic acid sequence set forth in SEQ ID NO: 3.

In some aspects, a promoter sequence can comprise the nucleic acid sequence set forth in SEQ ID NO: 8.

In some aspects, a polyA sequence can comprise the nucleic acid sequence set forth in SEQ ID NO: 9.

In some aspects, an rAAV vector can comprise in the 5' to 3' direction: a) a first AAV ITR sequence; b) a promoter sequence comprising the nucleic acid sequence set forth in SEQ ID NO: 8; c) a transgene nucleic acid molecule, wherein the transgene nucleic acid molecule comprises a nucleic acid sequence encoding for a GAN polypeptide, wherein the nucleic acid sequence encoding for a GAN polypeptide comprises the nucleic acid sequence set forth in SEQ ID NO: 3; d) a polyA sequence comprising the nucleic acid sequence set forth in SEQ ID NO: 9; and e) a second AAV ITR sequence.

In some aspects, an rAAV vector can comprise the nucleic acid sequence set forth in SEQ ID NO: 10.

In some aspects, an AAV capsid protein can be an AAV9 capsid protein.

In some aspects, an rAAV viral vector can be administered in an amount of about $3.5 \times 10^{13}$ to about $3.5 \times 10^{14}$ viral particles.

In some aspects, a subject can have been previously administered at least one therapeutically effective amount of an initial rAAV viral vector. In some aspects, an initial rAAV viral vector can have been administered to a subject intravenously, intrathecally, intracerebrally, intraventricularly, intranasally, intratracheally, intra-aurally, intra-ocularly, or peri-ocularly, orally, rectally, transmucosally, inhalationally, transdermally, parenterally, subcutaneously, intradermally, intramuscularly, intracisternally, intranervally, intrapleurally, topically, intralymphatically, intracisternally or intra-nerve. In some aspects, an initial rAAV viral vector can have been administered to a subject intrathecally.

In some aspects, an initial rAAV viral vector can be the same rAAV viral vector that is administered via injection into a vagus nerve of the subject.

In some aspects, a subject can have neutralizing antibodies against the rAAV viral vector.

The present disclosure provides a method of treating Giant Axonal Neuropathy in a subject comprising: a) intrathecally administering a first therapeutically effective amount of an rAAV viral vector to the subject and b) administering an at least second therapeutically effective amount of the rAAV viral vector by injecting the at least second therapeutically effective amount of the rAAV viral vector into the left vagus nerve of the subject, wherein the rAAV viral vector comprises: (i) an AAV9 capsid protein; and (ii) an rAAV vector, wherein the rAAV vector comprises the nucleic acid sequence put forth in SEQ ID NO: 10. In some aspects, a first therapeutically effective amount of the rAAV viral vector and an at least second therapeutically effective amount of the rAAV viral vector can be administered sequentially. In some aspects, a first therapeutically effective amount of the rAAV viral vector and an at least second therapeutically effective amount of the rAAV viral vector can be administered concurrently.

Any of the above aspects, or any other aspect described herein, can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The above and further features will be more clearly appreciated from the following detailed description when taken in conjunction with the accompanying drawings.

DETAILED DESCRIPTION

Figure 1:
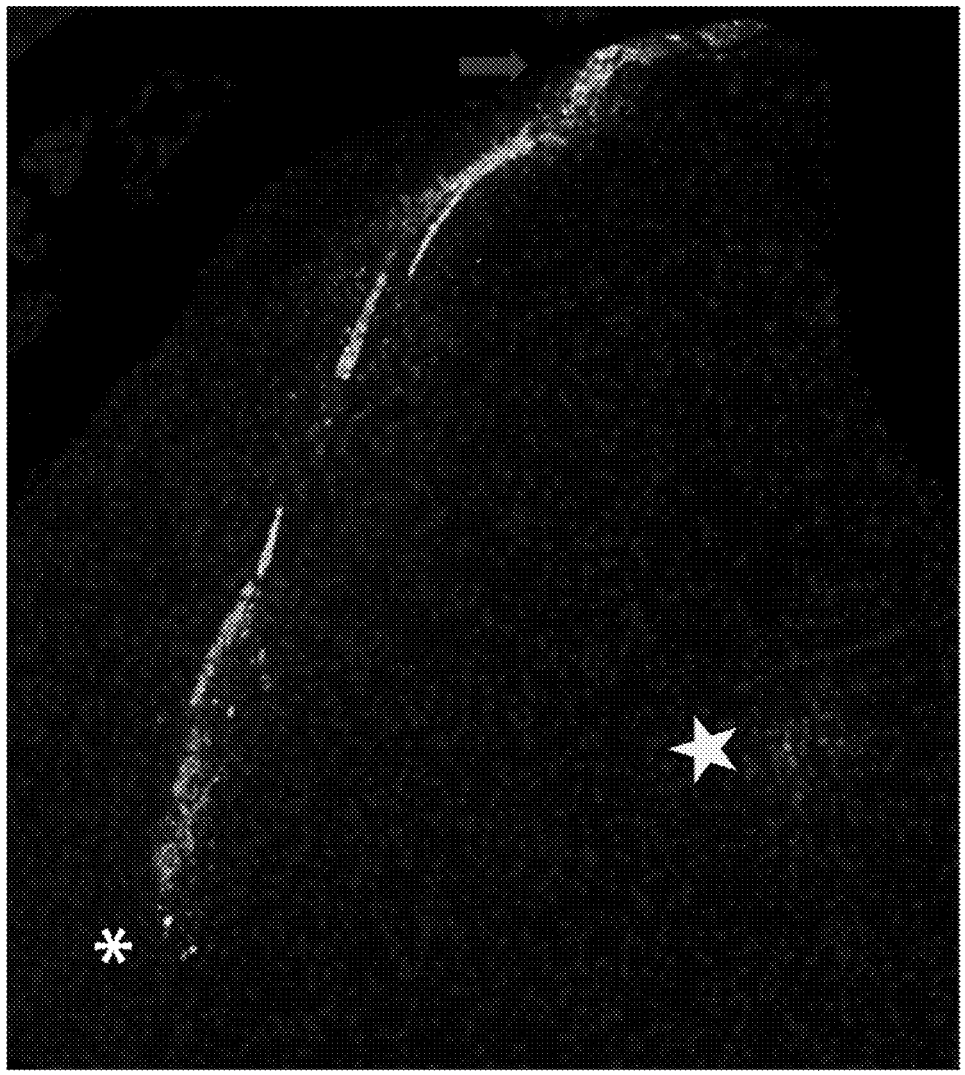
FIG. 1 is an image showing AAV9/Vector transgene expression using a GFP reporter protein following injection into the left vagus nerve of a rat. Arrow=vagus nerve; asterix=dorsal motor nucleus of the vagus; star=nucleus ambiguous.

The present disclosure provides, inter alia, compositions and methods for treating a disease in a subject, the method comprising administering at least one therapeutically effective amount of a recombinant adeno-associated virus (rAAV) viral vector to the subject via injection into a vagus nerve of the subject.

The present disclosure also provides, inter alia, isolated polynucleotides, recombinant adeno-associated virus (rAAV) vectors, and rAAV viral vectors comprising transgene nucleic acid molecules comprising nucleic acid sequences encoding for gigaxonin (GAN) polypeptides. The present disclosure also provides methods of manufacturing these isolated polynucleotides, rAAV vectors, and rAAV viral vectors, as well as their use to deliver transgenes to treat or prevent a disease or disorder, including diseases associated with loss, misfunction and/or deficiency of a GAN gene, including, but not limited to Giant Axonal Neuropathy.

Gigaxonin (GAN), also known as kelch-like protein 16, is a protein in humans that is encoded by the GAN gene. GAN is a member of the cytoskeletal BTB/kelch (Broad-Complex, Tramtrack and Bric a brac) family of proteins. GAN is an E3 ligase adaptor protein that promotes the ubiquitination and degradation of intermediate filament (IF) proteins. Mutations in the GAN gene have been shown to cause the Giant Axonal Neuropathy.

The term "adeno-associated virus" or "AAV" as used herein refers to a member of the class of viruses associated with this name and belonging to the genus Dependoparvovirus, family Parvoviridae. Adeno-associated virus is a single-stranded DNA virus that grows in cells in which certain functions are provided by a co-infecting helper virus. General information and reviews of AAV can be found in, for example, Carter, 1989, Handbook of Parvoviruses, Vol. 1, pp. 169-228, and Berns, 1990, Virology, pp. 1743-1764, Raven Press, (New York). It is fully expected that the same principles described in these reviews will be applicable to additional AAV serotypes characterized after the publication dates of the reviews because it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3: 1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control. Multiple serotypes of this virus are known to be suitable for gene delivery; all known serotypes can infect cells from various tissue types. At least 11 sequentially numbered AAV serotypes are known in the art. Non-limiting exemplary serotypes useful in the methods disclosed herein include any of the 11 serotypes, e.g., AAV2, AAV8, AAV9, or variant serotypes, e.g., AAV-DJ and AAV PHP.B. The AAV particle comprises, consists essentially of, or consists of three major viral proteins: VP1, VP2 and VP3. In some aspects, the AAV refers to the serotype AAV1, AAV2, AAV4, AAV5, AAV6, AAV7, AAV8, AAV9, AAV10, AAV11, AAV12, AAV13, AAVPHP.B, AAVrh74 or AAVrh.10.

Exemplary adeno-associated viruses and recombinant adeno-associated viruses include, but are not limited to all serotypes (e.g., AAV1, AAV2, AAV3, AAV4, AAV5, AAV6, AAV7, AAV8, AAV9, AAV10, AAV11, AAV12, AAV13, AAVPHP.B, AAVrh74 and AAVrh.10). Exemplary adeno-associated viruses and recombinant adeno-associated viruses include, but are not limited to, self-complementary AAV (scAAV) and AAV hybrids containing the genome of one serotype and the capsid of another serotype (e.g., AAV2/5, AAV-DJ and AAV-DJ8). Exemplary adeno-associated viruses and recombinant adeno-associated viruses include, but are not limited to, rAAV-LK03, AAV-KP-1 (described in detail in Kerun et al. JCI Insight, 2019; 4(22):e131610) and AAV-NP59 (described in detail in Paulk et al. Molecular Therapy, 2018; 26(1): 289-303).

AAV Structure and Function

AAV is a replication-deficient parvovirus, the single-stranded DNA genome of which is about 4.7 kb in length, including two 145-nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_001862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). The sequence of the AAV rh.74 genome is provided in U.S. Pat. No. 9,434,928. U.S. Pat. No. 9,434,928 also provides the sequences of the capsid proteins and a self-complementary genome. In one aspect, an AAV genome is a self-complementary genome. Cis-acting sequences directing viral DNA replication (rep), encapsidation/packaging, and host cell chromosome integration are contained within AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome.

The cap gene is expressed from the p40 promoter and encodes the three capsid proteins, VP1, VP2, and VP3. Alternative splicing and non-consensus translational start sites are responsible for the production of the three related capsid proteins. More specifically, after the single mRNA from which each of the VP1, VP2 and VP3 proteins are translated is transcribed, it can be spliced in two different manners: either a longer or shorter intron can be excised, resulting in the formation of two pools of mRNAs: a 2.3 kb- and a 2.6 kb-long mRNA pool. The longer intron is often preferred and thus the 2.3-kb-long mRNA can be called the major splice variant. This form lacks the first AUG codon, from which the synthesis of VP1 protein starts, resulting in a reduced overall level of VP1 protein synthesis. The first AUG codon that remains in the major splice variant is the initiation codon for the VP3 protein. However, upstream of that codon in the same open reading frame lies an ACG sequence (encoding threonine) which is surrounded by an optimal Kozak (translation initiation) context. This contributes to a low level of synthesis of the VP2 protein, which is actually the VP3 protein with additional N terminal residues, as is VP1, as described in Becerra S P et al., (December 1985). "Direct mapping of adeno-associated virus capsid proteins B and C: a possible ACG initiation codon". Proceedings of the National Academy of Sciences of the United States of America. 82 (23): 7919-23, Cassinotti P et al., (November 1988). "Organization of the adeno-associated virus (AAV) capsid gene: mapping of a minor spliced mRNA coding for virus capsid protein 1". Virology. 167 (1): 176-84, Muralidhar S et al., (January 1994). "Site-directed mutagenesis of adeno-associated virus type 2 structural protein initiation codons: effects on regulation of synthesis and biological activity". Journal of Virology. 68 (1): 170-6, and Trempe J P, Carter B J (September 1988). "Alternate mRNA splicing is required for synthesis of adeno-associated virus VP1 capsid protein". Journal of Virology. 62 (9): 3356-63, each of which is herein incorporated by reference. A single consensus polyA site is located at map position 95 of the AAV genome. The life cycle and genetics of AAV are reviewed in Muzyczka, Current Topics in Microbiology and Immunology, 158: 97-129 (1992).

Each VP1 protein contains a VP1 portion, a VP2 portion and a VP3 portion. The VP1 portion is the N-terminal portion of the VP1 protein that is unique to the VP1 protein. The VP2 portion is the amino acid sequence present within the VP1 protein that is also found in the N-terminal portion of the VP2 protein. The VP3 portion and the VP3 protein have the same sequence. The VP3 portion is the C-terminal portion of the VP1 protein that is shared with the VP1 and VP2 proteins.

The VP3 protein can be further divided into discrete variable surface regions I-IX (VR-I-IX). Each of the variable surface regions (VRs) can comprise or contain specific amino acid sequences that either alone or in combination with the specific amino acid sequences of each of the other VRs can confer unique infection phenotypes (e.g., decreased antigenicity, improved transduction and/or tissue-specific tropism relative to other AAV serotypes) to a particular serotype as described in DiMatta et al., "Structural Insight into the Unique Properties of Adeno-Associated Virus Serotype 9" J. Virol., Vol. 86 (12): 6947-6958, June 2012, the contents of which are incorporated herein by reference.

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA to generate AAV vectors. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., Hum Gene Ther, 8: 659-669 (1997); Kessler et al., Proc Nat. Acad Sc. USA, 93: 14082-14087 (1996); and Xiao et al., J Virol, 70: 8098-8108 (1996). See also, Chao et al., Mol Ther, 2:619-623 (2000) and Chao et al., Mol Ther, 4:217-222 (2001). Moreover, because muscle is highly vascularized, recombinant AAV transduction has resulted in the appearance of transgene products in the systemic circulation following intramuscular injection as described in Herzog et al., Proc Natl Acad Sci USA, 94: 5804-5809 (1997) and Murphy et al., Proc Natl Acad Sci USA, 94: 13921-13926 (1997). Moreover, Lewis et al., J Virol, 76: 8769-8775 (2002) demonstrated that skeletal myofibers possess the necessary cellular factors for correct antibody glycosylation, folding, and secretion, indicating that muscle is capable of stable expression of secreted protein therapeutics. Recombinant AAV (rAAV) genomes of the invention comprise, consist essentially of, or consist of a nucleic acid molecule encoding a therapeutic protein (e.g., KCTD7) and one or more AAV ITRs flanking the nucleic acid molecule. Production of pseudotyped rAAV is disclosed in, for example, WO2001083692. Other types of rAAV variants, for example rAAV with capsid mutations, are also contemplated. See, e.g., Marsic et al., Molecular Therapy, 22(11): 1900-1909 (2014). The nucleotide sequences of the genomes of various AAV serotypes are known in the art.

Isolated Polynucleotides Comprising Transgene Sequences

The present disclosure provides isolated polynucleotides comprising at least one transgene nucleic acid molecule.

In some aspects, a transgene nucleic acid molecule can comprise a nucleic acid sequence encoding a GAN polypeptide, or at least one fragment thereof. In some aspects, a transgene nucleic acid molecule can comprise a nucleic acid sequence encoding a biological equivalent of a GAN polypeptide.

In some aspects, a GAN polypeptide comprises, consists essentially of, or consists of an amino acid sequence at least 65%, 70%, 75%, 80%, 85%, 90%, 95%, 96%, 97%, 98%, 99% or 100% (or any percentage in between) identical to the amino acid sequence put forth in SEQ ID NO: 1 or SEQ ID NO: 2, or a fragment thereof. In some aspects, a GAN polypeptide comprises, consists essentially of, or consists of an amino acid sequence at least 65%, 70%, 75%, 80%, 85%, 90%, 95%, 96%, 97%, 98%, 99% or 100% (or any percentage in between) identical to at least one portion of the amino acid sequence put forth in SEQ ID NO: 1, or a fragment thereof.

In some aspects, a nucleic acid sequence encoding a GAN polypeptide comprises, consists essentially of, or consists of a nucleic acid sequence at least 65%, 70%, 75%, 80%, 85%, 90%, 95%, 96%, 97%, 98%, 99% or 100% (or any percentage in between) identical to the nucleic acid sequence put forth in any one of SEQ ID NO: 3-6. In some aspects, a nucleic acid sequence encoding a GAN polypeptide comprises, consists essentially of, or consists of a nucleic acid sequence at least 65%, 70%, 75%, 80%, 85%, 90%, 95%, 96%, 97%, 98%, 99% or 100% (or any percentage in between) identical to the nucleic acid sequences put forth in SEQ ID NO: 3.

In some aspects, the nucleic acid sequence encoding a GAN polypeptide can be a codon optimized nucleic acid sequence that encodes for a GAN polypeptide. A codon optimized nucleic acid sequence encoding a GAN polypeptide can comprise, consist essentially of, or consist of a nucleic acid sequence that is no more than 65%, 70%, 75%, 80%, 85%, 90%, 95%, 96%, 97%, 98%, 99% (or any percentage in between) identical to the wildtype human nucleic acid sequence encoding the GAN polypeptide. As used herein, the "wildtype human nucleic acid sequence encoding the GAN polypeptide" refers to the nucleic acid sequence that encodes the GAN polypeptide in a human genome, as put forth in SEQ ID NO: 7. SEQ ID NOs: 3-6 are unique codon optimized nucleic acid sequences that encode for a GAN polypeptide.

In some aspects, a codon optimized nucleic acid sequence encoding a GAN polypeptide, such as those put forth in SEQ ID NOs: 3-6, can comprise no donor splice sites. In some aspects, a codon optimized nucleic acid sequence encoding a GAN polypeptide can comprise no more than about one, or about two, or about three, or about four, or about five, or about six, or about seven, or about eight, or about nine, or about ten donor splice sites. In some aspects, a codon optimized nucleic acid sequence encoding a GAN polypeptide comprises at least one, or at least two, or at least three, or at least four, or at least five, or at least six, or at least seven, or at least eight, or at least nine, or at least ten fewer donor splice sites as compared to the wildtype human nucleic acid sequence encoding the GAN polypeptide. Without wishing to be bound by theory, the removal of donor splice sites in the codon optimized nucleic acid sequence can unexpectedly and unpredictably increase expression of the GAN polypeptide in vivo, as cryptic splicing is prevented. Moreover, cryptic splicing may vary between different subjects, meaning that the expression level of the GAN polypeptide comprising donor splice sites may unpredictably vary between different subjects.

In some aspects, a codon optimized nucleic acid sequence encoding a GAN polypeptide, such as those put forth in SEQ ID NOs: 3-6, can have a GC content that differs from the GC content of the wildtype human nucleic acid sequence encoding the GAN polypeptide. In some aspects, the GC content of a codon optimized nucleic acid sequence encoding a GAN polypeptide is more evenly distributed across the entire nucleic acid sequence, as compared to the wildtype human nucleic acid sequence encoding the GAN polypeptide. Without wishing to be bound by theory, by more evenly distributing the GC content across the entire nucleic acid sequence, the codon optimized nucleic acid sequence exhibits a more uniform melting temperature ("Tm") across the length of the transcript. The uniformity of melting temperature results unexpectedly in increased expression of the codon optimized nucleic acid in a human subject, as transcription and/or translation of the nucleic acid sequence occurs with less stalling of the polymerase and/or ribosome.

In some aspects, the codon optimized nucleic acid sequence encoding a GAN polypeptide, such as those put forth in SEQ ID NOs: 3-6, exhibits at least 5%, at least 10%, at least 20%, at least 30%, at least 50%, at least 75%, at least 100%, at least 200%, at least 300%, at least 500%, or at least 1000% increased expression in a human subject relative to a wild-type or non-codon optimized nucleic acid sequence encoding an GAN polypeptide.

In some aspects, a GAN polypeptide can further comprise a protein tag. Without wishing to be bound by theory, the inclusion of a protein tag can allow for the detection and/or visualization of the exogenous GAN polypeptide. As would be appreciated by the skilled artisan, non-limiting examples of protein tags include Myc tags, poly-histidine tags, FLAG-tags, HA-tags, SBP-tags or any other protein tag known in the art.

AAV Vectors

In some aspects, the isolated polynucleotides comprising at least one transgene nucleic acid molecule described herein can be a recombinant AAV (rAAV) vector.

As used herein, the term "vector" refers to a nucleic acid comprising, consisting essentially of, or consisting of an intact replicon such that the vector may be replicated when placed within a cell, for example by a process of transfection, infection, or transformation. It is understood in the art that once inside a cell, a vector may replicate as an extra-chromosomal (episomal) element or may be integrated into a host cell chromosome. Vectors may include nucleic acids derived from retroviruses, adenoviruses, herpesvirus, baculoviruses, modified baculoviruses, papovaviruses, or otherwise modified naturally occurring viruses. Exemplary non-viral vectors for delivering nucleic acid include naked DNA; DNA complexed with cationic lipids, alone or in combination with cationic polymers; anionic and cationic liposomes; DNA-protein complexes and particles comprising, consisting essentially of, or consisting of DNA condensed with cationic polymers such as heterogeneous polylysine, defined-length oligopeptides, and polyethyleneimine, in some cases contained in liposomes; and the use of ternary complexes comprising, consisting essentially of, or consisting of a virus and polylysine-DNA.

With respect to general recombinant techniques, vectors that contain both a promoter and a cloning site into which a polynucleotide can be operatively linked are well known in the art. Such vectors are capable of transcribing RNA in vitro or in vivo, and are commercially available from sources such as Agilent Technologies (Santa Clara, Calif.) and Promega Biotech (Madison, Wis.). In order to optimize expression and/or in vitro transcription, it may be necessary to remove, add or alter 5' and/or 3' untranslated portions of cloned transgenes to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

An "rAAV vector" as used herein refers to a vector comprising, consisting essentially of, or consisting of one or more transgene nucleic acid molecules and one or more AAV inverted terminal repeat sequences (ITRs). Such AAV vectors can be replicated and packaged into infectious viral particles when present in a host cell that provides the functionality of rep and cap gene products; for example, by transfection of the host cell. In some aspects, AAV vectors contain a promoter, at least one nucleic acid that may encode at least one protein or RNA, and/or an enhancer and/or a terminator within the flanking ITRs that is packaged into the infectious AAV particle. The encapsidated nucleic acid portion may be referred to as the AAV vector genome. Plasmids containing rAAV vectors may also contain elements for manufacturing purposes, e.g., antibiotic resistance genes, origin of replication sequences etc., but these are not encapsidated and thus do not form part of the AAV particle.

In some aspects, an rAAV vector can comprise at least one transgene nucleic acid molecule. In some aspects, an rAAV vector can comprise at least one AAV inverted terminal (ITR) sequence. In some aspects, an rAAV vector can comprise at least one promoter sequence. In some aspects, an rAAV vector can comprise at least one enhancer sequence. In some aspects, an rAAV vector can comprise at least one polyA sequence. In some aspects, an rAAV vector can comprise a RepCap sequence.

In some aspects, an rAAV vector can comprise a first AAV ITR sequence, a promoter sequence, a transgene nucleic acid molecule and a second AAV ITR sequence. In some aspects, an rAAV vector can comprise, in the 5' to 3' direction, a first AAV ITR sequence, a promoter sequence, a transgene nucleic acid molecule and a second AAV ITR sequence.

In some aspects, an rAAV vector can comprise a first AAV ITR sequence, a promoter sequence, a transgene nucleic acid molecule, a polyA sequence and a second AAV ITR sequence. In some aspects, an rAAV vector can comprise, in the 5' to 3' direction, a first AAV ITR sequence, a promoter sequence, a transgene nucleic acid molecule, a polyA sequence and a second AAV ITR sequence.

In some aspects, an rAAV vector can comprise more than one transgene nucleic acid molecule. In some aspects, an rAAV vector can comprise at least two transgene nucleic acid molecules, such that the rAAV vector comprises a first transgene nucleic acid molecule and an at least second transgene nucleic acid molecule. In some aspects, the first and the at least second transgene nucleic acid molecule can comprise the same nucleic acid sequence. In some aspects, the first and the at least second transgene nucleic acid molecules can comprise different nucleic acid sequences. In some aspects, the first and the at least second transgene nucleic acid sequences can be adjacent to each other.

In some aspects, an rAAV vector can comprise more than one promoter sequence. In some aspects, an rAAV vector can comprise at least two promoter sequences, such that the rAAV vector comprises a first promoter sequence and an at least second promoter sequence. In some aspects, the first and the at least second promoter sequences can comprise the same sequence. In some aspects, the first and the at least second promoter sequences can comprise different sequences. In some aspects, the first and the at least second promoter sequences can be adjacent to each other. In some aspects wherein an rAAV vector also comprises a first transgene nucleic acid molecule and an at least second transgene nucleic acid molecule, the first promoter can be located upstream (5') of the first transgene nucleic acid molecule and the at least second promoter can be located between the first transgene nucleic acid molecule and the at least second transgene nucleic acid molecule, such that the at least second promoter is downstream (3') of the first transgene nucleic acid molecule and upstream (5') of the at least second transgene nucleic acid molecule.

Any of the preceding rAAV vectors can further comprise at least one enhancer. The at least one enhancer can be located anywhere in the rAAV vector. In some aspects, the at least one enhancer can be located immediately upstream (5') of a promoter. Thus, an rAAV vector can comprise, in the 5' to 3' direction, a first AAV ITR sequence, an enhancer, a promoter sequence, a transgene nucleic acid molecule, a polyA sequence, and a second AAV ITR sequence. In some aspects, the at least one enhancer can be located immediately downstream (3') of a promoter. Thus, an rAAV vector can comprise, in the 5' to 3' direction, a first AAV ITR sequence, a promoter sequence, an enhancer, a transgene nucleic acid molecule, a polyA sequence, and a second AAV ITR sequence. In some aspects, the at least one enhancer can be located immediately downstream of a transgene nucleic acid molecule. Thus, an rAAV vector can comprise, in the 5' to 3' direction, a first AAV ITR sequence, a promoter sequence, a transgene nucleic acid molecule, an enhancer, a polyA sequence, and a second AAV ITR sequence.

AAV ITR Sequences

In some aspects, an AAV ITR sequence can comprise any AAV ITR sequence known in the art. In some aspects, an AAV ITR sequence can be an AAV1 ITR sequence, an AAV2 ITR sequence, an AAV4 ITR sequence, an AAV5 ITR sequence, an AAV6 ITR sequence, an AAV7 ITR sequence, an AAV8 ITR sequence, an AAV9 ITR sequence, an AAV10 ITR sequence, an AAV11 ITR sequence, an AAV12 ITR sequence, an AAV13 ITR sequence, an AAVrh74 ITR sequence or an AAVrh.10 ITR sequence.

Thus, in some aspects, an AAV ITR sequence can comprise, consist essentially of, or consist of an AAV1 ITR sequence, an AAV2 ITR sequence, an AAV4 ITR sequence, an AAV5 ITR sequence, an AAV6 ITR sequence, an AAV7 ITR sequence, an AAV8 ITR sequence, an AAV9 ITR sequence, an AAV10 ITR sequence, an AAV11 ITR sequence, an AAV12 ITR sequence, an AAV13 ITR sequence, an AAVrh74 ITR sequence, or an AAVrh.10 ITR sequence.

Promoter Sequence and Enhancers

The term "promoter" and "promoter sequence" as used herein means a control sequence that is a region of a polynucleotide sequence at which the initiation and rate of transcription of a coding sequence, such as a gene or a transgene, are controlled. Promoters may be constitutive, inducible, repressible, or tissue-specific, for example. Promoters may contain genetic elements at which regulatory proteins and molecules such as RNA polymerase and transcription factors may bind. Non-limiting exemplary promoters include Rous sarcoma virus (RSV) LTR promoter (optionally with the RSV enhancer), a cytomegalovirus (CMV) promoter, an SV40 promoter, a dihydrofolate reductase promoter, a β-actin promoter, a phosphoglycerol kinase (PGK) promoter, a U6 promoter, a synapsin promoter, an H1 promoter, a ubiquitous chicken β-actin hybrid (CBh) promoter, a small nuclear RNA (U1a or U1b) promoter, an MECP2 promoter, an MeP418 promoter, an MeP426 promoter, a human variant of the MeP426 promoter, a minimal MECP2 promoter, a VMD2 promoter, an mRho promoter, or an EF1 promoter.

Additional non-limiting exemplary promoters provided herein include, but are not limited to EF1a, Ubc, human β-actin, CAG, TRE, Ac5, Polyhedrin, CaMKIIa, Gall, TEF1, GDS, ADH1, Ubi, and α-1-antitrypsin (hAAT). It is known in the art that the nucleotide sequences of such promoters may be modified in order to increase or decrease the efficiency of mRNA transcription. See, e.g., Gao et al. (2018) Mol. Ther.: Nucleic Acids 12:135-145 (modifying TATA box of 7SK, U6 and H1 promoters to abolish RNA polymerase III transcription and stimulate RNA polymerase II-dependent mRNA transcription). Synthetically-derived promoters may be used for ubiquitous or tissue specific expression. Further, virus-derived promoters, some of which are noted above, may be useful in the methods disclosed herein, e.g., CMV, HIV, adenovirus, and AAV promoters. In some aspects, the promoter is used together with at least one enhancer to increase the transcription efficiency. Non-limiting examples of enhancers include an interstitial retinoid-binding protein (IRBP) enhancer, an RSV enhancer or a CMV enhancer.

In some aspects, a promoter sequence can comprise, consist essentially of, or consist of a Rous sarcoma virus (RSV) LTR promoter sequence (optionally with the RSV enhancer), a cytomegalovirus (CMV) promoter sequence, an SV40 promoter sequence, a dihydrofolate reductase promoter sequence, a JeT promoter sequence, a strong a β-actin promoter sequence, a phosphoglycerol kinase (PGK) promoter sequence, a U6 promoter sequence, synapsin promoter, an H1 promoter sequence, a ubiquitous chicken β-actin hybrid (CBh) promoter sequence, a small nuclear RNA (U1a or U1b) promoter sequence, an MECP2 promoter sequence, an MeP418 promoter, an MeP426 promoter sequence, a small ubiquitous promoter sequence (also known as a JetI promoter sequence) MECP2 promoter sequence, a VMD2 promoter sequence, an mRho promoter sequence, an EFI promoter sequence, an EFla promoter sequence, a Ubc promoter sequence, a human β-actin promoter sequence, a CAG promoter sequence, a TRE promoter sequence, an Ac5 promoter sequence, a Polyhedrin promoter sequence, a CaMKIIa promoter sequence, a Gall promoter sequence, a TEF1 promoter sequence, a GDS promoter sequence, an ADH1 promoter sequence, a Ubi promoter sequence, a MeP426 promoter, or an α-1-antitrypsin (hAAT) promoter sequence.

An enhancer is a regulatory element that increases the expression of a target sequence. A "promoter/enhancer" is a polynucleotide that contains sequences capable of providing both promoter and enhancer functions. For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) or synthetic techniques such that transcription of that gene is directed by the linked enhancer/promoter. Non-limiting examples of linked enhancer/promoter for use in the methods, compositions and constructs provided herein include a PDE promoter plus IRBP enhancer or a CMV enhancer plus U1a promoter. It is understood in the art that enhancers can operate from a distance and irrespective of their orientation relative to the location of an endogenous or heterologous promoter. It is thus further understood that an enhancer operating at a distance from a promoter is thus "operably linked" to that promoter irrespective of its location in the vector or its orientation relative to the location of the promoter.

As used throughout the disclosure, the term "operably linked" refers to the expression of a gene (i.e. a transgene) that is under the control of a promoter with which it is spatially connected. A promoter can be positioned 5' (upstream) or 3' (downstream) of a gene under its control. A promoter can be positioned 5'(upstream) of a gene under its control. The distance between a promoter and a gene can be approximately the same as the distance between that promoter and the gene it controls in the gene from which the promoter is derived. Variation in the distance between a promoter and a gene can be accommodated without loss of promoter function.

In some aspects, a promoter sequence can comprise, consist essentially of, or consist of a JeT promoter sequence. A JeT promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to the nucleic acid sequence put forth in SEQ ID NO: 8.

Transgene Nucleic Acid Molecules

Transgene nucleic acid molecules can comprise, consist essentially of, or consist of any of the transgene nucleic acid molecules described above under the heading "isolated polynucleotides comprising transgene sequences".

In some aspects, a transgene nucleic acid molecule present in an rAAV vector can be under transcriptional control of a promoter sequence also present in the same rAAV vector.

polyA Sequences

In some aspects, a polyadenylation (polyA) sequence can comprise any polyA sequence known in the art. Non-limiting examples of polyA sequences include, but are not limited to, an MECP2 polyA sequence, a retinol dehydrogenase 1 (RDH1) polyA sequence, a bovine growth hormone (BGH) polyA sequence, an SV40 polyA sequence, a SPA49 polyA sequence, a sNRP-TK65 polyA sequence, a sNRP polyA sequence, or a TK65 polyA sequence.

Thus, a polyA sequence can comprise, consist essentially of, or consist of an MeCP2 polyA sequence, a retinol dehydrogenase 1 (RDH1) polyA sequence, a bovine growth hormone (BGH) polyA sequence, an SV40 polyA sequence, a SPA49 polyA sequence, a sNRP-TK65 polyA sequence, a sNRP polyA sequence, or a TK65 polyA sequence.

In some aspects, a polyA sequence can comprise, consist essentially of, or consist of a nucleic acid sequence at least 65%, 70%, 75%, 80%, 85%, 90%, 95%, 96%, 97%, 98%, 99% or 100% (or any percentage in between) identical the sequence put forth in SEQ ID NO: 9.

In some aspects, an rAAV vector of the present disclosure can comprise, consist essentially of, or consist of a nucleic acid sequence at least 65%, 70%, 75%, 80%, 85%, 90%, 95%, 96%, 97%, 98%, 99% or 100% (or any percentage in between) identical to the sequence put forth in SEQ ID NO: 10.

In some aspects, an rAAV vector of the present disclosure can comprise, consist essentially of, or consist of a nucleic acid sequence at least 65%, 70%, 75%, 80%, 85%, 90%, 95%, 96%, 97%, 98%, 99% or 100% (or any percentage in between) identical to the sequence put forth in SEQ ID NO: 11.

Bacterial Plasmids

In some aspects, the rAAV vectors of the present disclosure can be contained within a bacterial plasmid to allow for propagation of the rAAV vector in vitro. Thus, the present disclosure provides bacterial plasmids comprising any of the rAAV vectors described herein. A bacterial plasmid can further comprise an origin of replication sequence. A bacterial plasmid can further comprise an antibiotic resistance gene. A bacterial plasmid can further comprise a resistance gene promoter. A bacterial plasmid can further comprise a prokaryotic promoter. In some aspects, a bacterial plasmid of the present disclosure can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the nucleic acid sequence put forth in SEQ ID NO: 10 or SEQ ID NO: 11.

Origin of Replication Sequence

In some aspects, an origin of replication sequence can comprise, consist essentially of, or consist of any origin of replication sequence known in the art. The origin of replication sequence can be a bacterial origin of replication sequence, thereby allowing the rAAV vector comprising said bacterial origin of replication sequence to be produced, propagated and maintained in bacteria, using methods standard in the art.

Antibiotic Resistance Genes

In some aspects, bacterial plasmids, rAAV vectors and/or rAAV viral vectors of the disclosure can comprise an antibiotic resistance gene.

In some aspects, an antibiotic resistance gene can comprise, consist essentially of, or consist of any antibiotic resistance genes known in the art. Examples of antibiotic resistance genes known in the art include, but are not limited to kanamycin resistance genes, spectinomycin resistance genes, streptomycin resistance genes, ampicillin resistance genes, carbenicillin resistance genes, bleomycin resistance genes, erythromycin resistance genes, polymyxin B resistance genes, tetracycline resistance genes and chloramphenicol resistance genes.

AAV Viral Vectors

A "viral vector" is defined as a recombinantly produced virus or viral particle that contains a polynucleotide to be delivered into a host cell, either in vivo, ex vivo or in vitro. Examples of viral vectors include retroviral vectors, AAV vectors, lentiviral vectors, adenovirus vectors, alphavirus vectors and the like. Alphavirus vectors, such as Semliki Forest virus-based vectors and Sindbis virus-based vectors, have also been developed for use in gene therapy and immunotherapy. See, e.g., Schlesinger and Dubensky (1999) Curr. Opin. Biotechnol. 5:434-439 and Ying, et al. (1999) Nat. Med. 5(7):823-827.

An "AAV virion" or "AAV viral particle" or "AAV viral vector" or "rAAV viral vector" or "AAV vector particle" or "AAV particle" refers to a viral particle composed of at least one AAV capsid protein and an encapsidated polynucleotide rAAV vector. Thus, production of an rAAV viral vector necessarily includes production of an rAAV vector, as such a vector is contained within an rAAV vector.

As used herein, the term "viral capsid" or "capsid" refers to the proteinaceous shell or coat of a viral particle. Capsids function to encapsidate, protect, transport, and release into the host cell a viral genome. Capsids are generally comprised of oligomeric structural subunits of protein ("capsid proteins"). As used herein, the term "encapsidated" means enclosed within a viral capsid. The viral capsid of AAV is composed of a mixture of three viral capsid proteins: VP1, VP2, and VP3. The mixture of VP1, VP2 and VP3 contains 60 monomers that are arranged in a T=1 icosahedral symmetry in a ratio of 1:1:10 (VP1:VP2:VP3) or 1:1:20 (VP1:VP2:VP3) as described in Sonntag F et al., (June 2010). "A viral assembly factor promotes AAV2 capsid formation in the nucleolus". Proceedings of the National Academy of Sciences of the United States of America. 107 (22): 10220-5, and Rabinowitz J E, Samulski R J (December 2000). "Building a better vector: the manipulation of AAV virions". Virology. 278 (2): 301-8, each of which is incorporated herein by reference in its entirety.

The present disclosure provides an rAAV viral vector comprising: a) any of the rAAV vectors described herein, or complement thereof; and b) an AAV capsid protein.

The present disclosure provides an rAAV viral vector comprising: a) any of the rAAV vectors described herein; and b) an AAV capsid protein.

An AAV capsid protein can be any AAV capsid protein known in the art. An AAV capsid protein can be an AAV1 capsid protein, an AAV2 capsid protein, an AAV4 capsid protein, an AAV5 capsid protein, an AAV6 capsid protein, an AAV7 capsid protein, an AAV8 capsid protein, an AAV9 capsid protein, an AAV10 capsid protein, an AAV11 capsid protein, an AAV12 capsid protein, an AAV13 capsid protein, an AAVPHP.B capsid protein, an AAVrh74 capsid protein or an AAVrh.10 capsid protein.

Alternative rAAV Vector and rAAV Viral Vector Embodiments

1. An rAAV vector, comprising, in the 5' to 3' direction
   a) a first AAV ITR sequence;
   b) a promoter sequence;
   c) a transgene nucleic acid molecule, wherein the transgene nucleic acid molecule comprises a nucleic acid sequence encoding for a GAN polypeptide;
   d) a polyA sequence; and
   e) a second AAV ITR sequence.

2. The rAAV vector of embodiment 1, wherein the GAN polypeptide comprises the amino acid sequence set forth in SEQ ID NO: 1 or SEQ ID NO: 2.

3. The rAAV vector of embodiment 2, wherein the KCTD7 polypeptide comprises the amino acid sequence set forth in SEQ ID NO: 1.

4. The rAAV vector of embodiment 2, wherein the KCTD7 polypeptide comprises the amino acid sequence set forth in SEQ ID NO: 2.

5. The rAAV vector of any one of the preceding embodiments, wherein the nucleic acid sequence encoding for a GAN polypeptide comprises the nucleic acid sequence set forth in any one of SEQ ID NOs: 3-6.

6. The rAAV vector of any one of the preceding embodiments, wherein the nucleic acid sequence encoding for a GAN polypeptide comprises the nucleic acid sequence set forth in SEQ ID NO: 3.

7. The rAAV vector of any one of the preceding embodiments, wherein the nucleic acid sequence encoding for a GAN polypeptide comprises the nucleic acid sequence set forth in SEQ ID NO: 4.

8. The rAAV vector of any one of the preceding embodiments, wherein the nucleic acid sequence encoding for a GAN polypeptide comprises the nucleic acid sequence set forth in SEQ ID NO: 5.

9. The rAAV vector of any one of the preceding embodiments, wherein the nucleic acid sequence encoding for a GAN polypeptide comprises the nucleic acid sequence set forth in SEQ ID NO: 6.

10. The rAAV vector of any one of the preceding embodiments, wherein the first AAV ITR sequence comprises an AAV1 ITR sequence, an AAV2 ITR sequence, an AAV4 ITR sequence, an AAV5 ITR sequence, an AAV6 ITR sequence, an AAV7 ITR sequence, an AAV8 ITR sequence, an AAV9 ITR sequence, an AAV10 ITR sequence, an AAV11 ITR sequence, an AAV12 ITR sequence, an AAV13 ITR sequence, an AAVrh74 ITR sequence, an AAVrh.10 ITR sequence or any combination thereof.

11. The rAAV vector of any one of the preceding embodiments, wherein the first AAV ITR sequence comprises an AAV1 ITR sequence.

12. The rAAV vector of any one of the preceding embodiments, wherein the first AAV ITR sequence comprises an AAV2 ITR sequence.

13. The rAAV vector of any one of the preceding embodiments, wherein the first AAV ITR sequence comprises an AAV4 ITR sequence.

14. The rAAV vector of any one of the preceding embodiments, wherein the first AAV ITR sequence comprises an AAV5 ITR sequence.

15. The rAAV vector of any one of the preceding embodiments, wherein the first AAV ITR sequence comprises an AAV6 ITR sequence.

16. The rAAV vector of any one of the preceding embodiments, wherein the first AAV ITR sequence comprises an AAV7 ITR sequence.

17. The rAAV vector of any one of the preceding embodiments, wherein the first AAV ITR sequence comprises an AAV8 ITR sequence.

18. The rAAV vector of any one of the preceding embodiments, wherein the first AAV ITR sequence comprises an AAV9 ITR sequence.

19. The rAAV vector of any one of the preceding embodiments, wherein the first AAV ITR sequence comprises an AAV10 ITR sequence.

20. The rAAV vector of any one of the preceding embodiments, wherein the first AAV ITR sequence comprises an AAV11 ITR sequence.

21. The rAAV vector of any one of the preceding embodiments, wherein the first AAV ITR sequence comprises an AAV12 ITR sequence.

22. The rAAV vector of any one of the preceding embodiments, wherein the first AAV ITR sequence comprises an AAV13 ITR sequence.

23. The rAAV vector of any one of the preceding embodiments, wherein the first AAV ITR sequence comprises an AAVrh74 ITR sequence.

24. The rAAV vector of any one of the preceding embodiments, wherein the first AAV ITR sequence comprises an AAVrh.10 ITR sequence.

25. The rAAV vector of any one of the preceding embodiments, wherein the second AAV ITR sequence comprises an AAV1 ITR sequence, an AAV2 ITR sequence, an AAV4 ITR sequence, an AAV5 ITR sequence, an AAV6 ITR sequence, an AAV7 ITR sequence, an AAV8 ITR sequence, an AAV9 ITR sequence, an AAV10 ITR sequence, an AAV11 ITR sequence, an AAV12 ITR sequence, an AAV13 ITR sequence, an AAVrh74 ITR sequence, an AAVrh.10 ITR sequence or any combination thereof.

26. The rAAV vector of any one of the preceding embodiments, wherein the second AAV ITR sequence comprises an AAV1 ITR sequence.

27. The rAAV vector of any one of the preceding embodiments, wherein the second AAV ITR sequence comprises an AAV2 ITR sequence.

28. The rAAV vector of any one of the preceding embodiments, wherein the second AAV ITR sequence comprises an AAV4 ITR sequence.

29. The rAAV vector of any one of the preceding embodiments, wherein the second AAV ITR sequence comprises an AAV5 ITR sequence.

30. The rAAV vector of any one of the preceding embodiments, wherein the second AAV ITR sequence comprises an AAV6 ITR sequence.

31. The rAAV vector of any one of the preceding embodiments, wherein the second AAV ITR sequence comprises an AAV7 ITR sequence.

32. The rAAV vector of any one of the preceding embodiments, wherein the second AAV ITR sequence comprises an AAV8 ITR sequence.

33. The rAAV vector of any one of the preceding embodiments, wherein the second AAV ITR sequence comprises an AAV9 ITR sequence.

34. The rAAV vector of any one of the preceding embodiments, wherein the second AAV ITR sequence comprises an AAV10 ITR sequence.

35. The rAAV vector of any one of the preceding embodiments, wherein the second AAV ITR sequence comprises an AAV11 ITR sequence.

36. The rAAV vector of any one of the preceding embodiments, wherein the second AAV ITR sequence comprises an AAV12 ITR sequence.

37. The rAAV vector of any one of the preceding embodiments, wherein the second AAV ITR sequence comprises an AAV13 ITR sequence.

38. The rAAV vector of any one of the preceding embodiments, wherein the second AAV ITR sequence comprises an AAVrh74 ITR sequence.

39. The rAAV vector of any one of the preceding embodiments, wherein the second AAV ITR sequence comprises an AAVrh.10 ITR sequence.

40. The rAAV vector of any one of the preceding embodiments, wherein the promoter sequence comprises a JeT promoter sequence.

41. The rAAV vector of any one of the preceding embodiments, wherein the JeT promoter sequence comprises the nucleic acid sequence set forth in SEQ ID NO: 8.

42. The rAAV vector of any one of the preceding embodiments, wherein the polyA sequence comprises the nucleic acid sequence set forth in SEQ ID NO: 11.

43. An rAAV vector of any one of the preceding embodiments, comprising, in the 5' to 3' direction
   a) a first AAV ITR sequence
   b) a promoter sequence comprising the nucleic acid sequence of SEQ ID NO: 8;
   c) a transgene nucleic acid molecule, wherein the transgene nucleic acid molecule comprises a nucleic acid sequence encoding for a GAN polypeptide, wherein the GAN polypeptide comprises the amino acid sequence of SEQ ID NO: 1 or SEQ ID NO: 2;
   d) a polyA sequence comprising the nucleic acid sequence of SEQ ID NO: 9; and
   e) a second AAV ITR sequence.

44. An rAAV vector of any one of the preceding embodiments, comprising, in the 5' to 3' direction
   a) a first AAV ITR sequence
   b) a promoter sequence comprising the nucleic acid sequence of SEQ ID NO: 8;
   c) a transgene nucleic acid molecule, wherein the transgene nucleic acid molecule comprises a nucleic acid sequence encoding for a GAN polypeptide, wherein the GAN polypeptide comprises the amino acid sequence of SEQ ID NO: 1;
   d) a polyA sequence comprising the nucleic acid sequence of SEQ ID NO: 9; and
   e) a second AAV ITR sequence.

45. An rAAV vector of any one of the preceding embodiments, comprising, in the 5' to 3' direction
   a) a first AAV ITR sequence
   b) a promoter sequence comprising the nucleic acid sequence of SEQ ID NO: 8;
   c) a transgene nucleic acid molecule, wherein the transgene nucleic acid molecule comprises a nucleic acid sequence encoding for a GAN polypeptide, wherein the GAN polypeptide comprises the amino acid sequence of SEQ ID NO: 2;
   d) a polyA sequence comprising the nucleic acid sequence of SEQ ID NO: 9; and
   e) a second AAV ITR sequence.

46. An rAAV vector of any one of the preceding embodiments, comprising, in the 5' to 3' direction
   a) a first AAV ITR sequence
   b) a promoter sequence comprising the nucleic acid sequence of SEQ ID NO: 8;
   c) a transgene nucleic acid molecule, wherein the transgene nucleic acid molecule comprises a nucleic acid sequence encoding for a GAN polypeptide, wherein the nucleic acid sequence encoding for a GAN polypeptide comprises the nucleic acid sequence set forth in any one of SEQ ID NOs: 3-6;
   d) a polyA sequence comprising the nucleic acid sequence of SEQ ID NO: 9; and
   e) a second AAV ITR sequence.

47. An rAAV vector of any one of the preceding embodiments, comprising, in the 5' to 3' direction
   a) a first AAV ITR sequence
   b) a promoter sequence comprising the nucleic acid sequence of SEQ ID NO: 8;
   c) a transgene nucleic acid molecule, wherein the transgene nucleic acid molecule comprises a nucleic acid sequence encoding for a GAN polypeptide, wherein the nucleic acid sequence encoding for a GAN polypeptide comprises the nucleic acid sequence set forth in any one of SEQ ID NOs: 3-6;
   d) a polyA sequence comprising the nucleic acid sequence of SEQ ID NO: 9; and
   e) a second AAV ITR sequence.

48. An rAAV vector of any one of the preceding embodiments, comprising, in the 5' to 3' direction
   a) a first AAV ITR sequence
   b) a promoter sequence comprising the nucleic acid sequence of SEQ ID NO: 8;
   c) a transgene nucleic acid molecule, wherein the transgene nucleic acid molecule comprises a nucleic acid sequence encoding for a GAN polypeptide, wherein the nucleic acid sequence encoding for a GAN polypeptide comprises the nucleic acid sequence set forth in SEQ ID NO: 3;
   d) a polyA sequence comprising the nucleic acid sequence of SEQ ID NO: 9; and
   e) a second AAV ITR sequence.

49. An rAAV vector of any one of the preceding embodiments, comprising, in the 5' to 3' direction
   a) a first AAV ITR sequence
   b) a promoter sequence comprising the nucleic acid sequence of SEQ ID NO: 8;
   c) a transgene nucleic acid molecule, wherein the transgene nucleic acid molecule comprises a nucleic acid sequence encoding for a GAN polypeptide, wherein the nucleic acid sequence encoding for a GAN polypeptide comprises the nucleic acid sequence set forth in SEQ ID NO: 4;
   d) a polyA sequence comprising the nucleic acid sequence of SEQ ID NO: 9; and
   e) a second AAV ITR sequence.

50. An rAAV vector of any one of the preceding embodiments, comprising, in the 5' to 3' direction
   a) a first AAV ITR sequence
   b) a promoter sequence comprising the nucleic acid sequence of SEQ ID NO: 8;
   c) a transgene nucleic acid molecule, wherein the transgene nucleic acid molecule comprises a nucleic acid sequence encoding for a GAN polypeptide, wherein the nucleic acid sequence encoding for a GAN polypeptide comprises the nucleic acid sequence set forth in SEQ ID NO: 5;
   d) a polyA sequence comprising the nucleic acid sequence of SEQ ID NO: 9; and
   e) a second AAV ITR sequence.

51. An rAAV vector of any one of the preceding embodiments, comprising, in the 5' to 3' direction
   a) a first AAV ITR sequence
   b) a promoter sequence comprising the nucleic acid sequence of SEQ ID NO: 8;
   c) a transgene nucleic acid molecule, wherein the transgene nucleic acid molecule comprises a nucleic acid sequence encoding for a GAN polypeptide, wherein the nucleic acid sequence encoding for a GAN polypeptide comprises the nucleic acid sequence set forth in SEQ ID NO: 6;
   d) a polyA sequence comprising the nucleic acid sequence of SEQ ID NO: 9; and
   e) a second AAV ITR sequence.

52. An rAAV vector of any one of the preceding embodiments, wherein the rAAV vector comprises the nucleic acid sequence of SEQ ID NO: 10.

53. An rAAV vector of any one of the preceding embodiments, wherein the rAAV vector comprises the nucleic acid sequence of SEQ ID NO: 11.

54. An rAAV viral vector comprising:
   a) an rAAV vector of any one of the preceding embodiments, or complement thereof; and
   b) an AAV capsid protein.

55. An rAAV viral vector comprising:
   a) an rAAV vector of any one of the preceding embodiments; and
   b) an AAV capsid protein.

56. The rAAV viral vector of embodiment 50 or 51, wherein the AAV capsid protein is an AAV1 capsid protein, an AAV2 capsid protein, an AAV4 capsid protein, an AAV5 capsid protein, an AAV6 capsid protein, an AAV7 capsid protein, an AAV8 capsid protein, an AAV5 capsid protein, an AAV10 capsid protein, an AAV11 capsid protein, an AAV12 capsid protein, an AAV13 capsid protein, an AAVPHP.B capsid protein, an AAVrh74 capsid protein or an AAVrh.10 capsid protein.

57. The rAAV viral vector of embodiment 52, wherein the AAV capsid protein is an AAV1 capsid protein.

58. The rAAV viral vector of embodiment 52, wherein the AAV capsid protein is an AAV2 capsid protein.

59. The rAAV viral vector of embodiment 52, wherein the AAV capsid protein is an AAV3 capsid protein.

60. The rAAV viral vector of embodiment 52, wherein the AAV capsid protein is an AAV4 capsid protein.

61. The rAAV viral vector of embodiment 52, wherein the AAV capsid protein is an AAV5 capsid protein.

62. The rAAV viral vector of embodiment 52, wherein the AAV capsid protein is an AAV6 capsid protein.

63. The rAAV viral vector of embodiment 52, wherein the AAV capsid protein is an AAV7 capsid protein.

64. The rAAV viral vector of embodiment 52, wherein the AAV capsid protein is an AAV8 capsid protein.

65. The rAAV viral vector of embodiment 52, wherein the AAV capsid protein is an AAV9 capsid protein.

66. The rAAV viral vector of embodiment 52, wherein the AAV capsid protein is an AAV10 capsid protein.

67. The rAAV viral vector of embodiment 52, wherein the AAV capsid protein is an AAV11 capsid protein.

68. The rAAV viral vector of embodiment 52, wherein the AAV capsid protein is an AAV12 capsid protein.

69. The rAAV viral vector of embodiment 52, wherein the AAV capsid protein is an AAV13 capsid protein.

70. The rAAV viral vector of embodiment 52, wherein the AAV capsid protein is an AAVPHP.B capsid protein.

71. The rAAV viral vector of embodiment 52, wherein the AAV capsid protein is an AAVrh74 capsid protein.

72. The rAAV viral vector of embodiment 52, wherein the AAV capsid protein is an AAVrh.10 capsid protein.

Compositions and Pharmaceutical Compositions

The present disclosure provides compositions comprising any of the isolated polynucleotides, rAAV vectors, and/or rAAV viral vectors described herein. In some aspects, the compositions can be pharmaceutical compositions. Accordingly, the present disclosure provides pharmaceutical compositions comprising any of the isolated polynucleotides, rAAV vectors, and/or rAAV viral vectors described herein.

The pharmaceutical composition, as described herein, may be formulated by any methods known or developed in the art of pharmacology, which include but are not limited to contacting the active ingredients (e.g., viral particles or recombinant vectors) with an excipient and/or additive and/or other accessory ingredient, dividing or packaging the product to a dose unit. The viral particles of this disclosure may be formulated with desirable features, e.g., increased stability, increased cell transfection, sustained or delayed release, biodistributions or tropisms, modulated or enhanced translation of encoded protein in vivo, and the release profile of encoded protein in vivo.

As such, the pharmaceutical composition may further comprise saline, lipidoids, liposomes, lipid nanoparticles, polymers, lipoplexes, core-shell nanoparticles, peptides, proteins, cells transfected with viral vectors (e.g., for transplantation into a subject), nanoparticle mimics or combinations thereof. In some aspects, the pharmaceutical composition is formulated as a nanoparticle. In some aspects, the nanoparticle is a self-assembled nucleic acid nanoparticle.

A pharmaceutical composition in accordance with the present disclosure may be prepared, packaged, and/or sold in bulk, as a single unit dose, and/or as a plurality of single unit doses. The amount of the active ingredient is generally equal to the dosage of the active ingredient which would be administered to a subject and/or a convenient fraction of such a dosage such as, for example, one-half or one-third of such a dosage. The formulations of the invention can include one or more excipients and/or additives, each in an amount that together increases the stability of the viral vector, increases cell transfection or transduction by the viral vector, increases the expression of viral vector encoded protein, and/or alters the release profile of viral vector encoded proteins. In some aspects, the pharmaceutical composition comprises an excipient and/or additive. Non limiting examples of excipients and/or additives include solvents, dispersion media, diluents, or other liquid vehicles, dispersion or suspension aids, surface active agents, isotonic agents, thickening or emulsifying agents, preservatives, or combination thereof.

In some aspects, the pharmaceutical composition comprises a cryoprotectant. The term "cryoprotectant" refers to an agent capable of reducing or eliminating damage to a substance during freezing. Non-limiting examples of cryoprotectants include sucrose, trehalose, lactose, glycerol, dextrose, raffinose and/or mannitol.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

In some aspects, a pharmaceutical composition of the present disclosure can comprise phosphate-buffered saline (PBS), D-sorbitol or any combination thereof.

In some aspects, a pharmaceutical composition can comprise PBS, wherein the PBS is present at a concentration of about 100 mM to about 500 mM, or about 200 mM to about 400 mM, or about 300 mM to about 400 mM. In some aspects, the sodium chloride can be present at a concentration of about 350 mM.

In some aspects, a pharmaceutical composition can comprise D-sorbitol, wherein the D-sorbitol is present at a concentration of about 1% to about 10%, or about 2.5% to about 7.5%. In some aspects, the D-sorbitol can be present at a concentration of about 5%.

Thus, the present disclosure provides a pharmaceutical composition comprising an rAAV vector and/or rAAV viral vector of the present disclosure in a 350 mM phosphate-buffered saline solution comprising D-sorbitol at a concentration of 5%.

Methods of Using the Compositions of the Disclosure

The present disclosure provides the use of a disclosed composition or pharmaceutical composition for the treatment of a disease or disorder in a cell, tissue, organ, animal, or subject, as known in the art or as described herein, using the disclosed compositions and pharmaceutical compositions, e.g., administering or contacting the cell, tissue, organ, animal, or subject with a therapeutic effective amount of the composition or pharmaceutical composition. In one aspect, the subject is a mammal. Preferably, the subject is human. The terms "subject" and "patient" are used interchangeably herein.

This disclosure provides methods of preventing or treating a disease and/or disorder, comprising, consisting essentially of, or consisting of administering to a subject a therapeutically effective amount of any one of the rAAV vectors, rAAV viral vectors, compositions and/or pharmaceutical compositions disclosed herein.

Methods of treatment can alleviate one or more symptoms of a disease and/or disorder described herein. In an embodiment, delivery of compositions described herein can prevent or delay development of detectable symptoms, if administered to a subject carrying a mutation in the GAN gene before symptoms become detectable. Therefore, treatment can be therapeutic or prophylactic. Therapy refers to inhibition or reversal of established symptoms or phenotype. Therapy can also mean delay of onset of symptoms or phenotype. Prophylaxis means inhibiting or preventing development of symptoms in subjects not already displaying overt symptoms. Subjects not displaying overt symptoms can be identified early in life as carrying a loss of function mutation in the GAN gene by appropriate genetic testing performed before 18 months, 12 months, or 6 months of age.

A subject to be treated using the methods, compositions, pharmaceutical compositions, rAAV vectors or rAAV viral vectors of the present disclosure can have any of the diseases and/or symptoms described herein.

The present disclosure provides a method of treating a disease and/or disorder in a subject comprising administering to the subject at least one therapeutically effective amount of a gene therapy (e.g. an rAAV viral vector) by injecting the at least one therapeutically effective amount of the gene therapy into a vagus nerve of the subject.

The present disclosure provides a method of treating a disease and/or disorder in a subject comprising administering to the subject at least one therapeutically effective amount of an rAAV viral vector by injecting the at least one therapeutically effective amount of the rAAV viral vector into a vagus nerve of the subject. The present disclosure provides at least one therapeutically effective amount of an rAAV viral vector for use in the treatment of a disease and/or disorder in the subject, wherein the rAAV viral vector is for administration to the subject via injection into a vagus nerve of the subject. The present disclosure provides the use of at least one therapeutically effective amount of an rAAV viral vector for the manufacture of a medicament for the treatment of a disease and/or disorder in a subject, wherein the at least one therapeutically effective amount of the rAAV viral vector is for administration to the subject via injection into a vagus nerve of the subject.

In some aspects, the vagus nerve is the left vagus nerve. Accordingly, the present disclosure provides a method of treating a disease and/or disorder in a subject comprising administering to the subject at least one therapeutically effective amount of an rAAV viral vector by injecting the at least one therapeutically effective amount of the rAAV viral vector into the left vagus nerve of the subject. The present disclosure also provides at least one therapeutically effective amount of an rAAV viral vector for use in the treatment of a disease and/or disorder in the subject, wherein the at least one therapeutically effective amount of the rAAV viral vector is for administration to the subject via injection into the left vagus nerve of the subject. The present disclosure also provides the use of at least one therapeutically effective amount of an rAAV viral vector for the manufacture of a medicament for the treatment of a disease and/or disorder in a subject, wherein the at least one therapeutically effective amount of the rAAV viral vector is for administration to the subject via injection into the left vagus nerve of the subject.

In some aspects, the vagus nerve is the right vagus nerve. Accordingly, the present disclosure provides a method of treating a disease and/or disorder in a subject comprising administering to the subject at least one therapeutically effective amount of an rAAV viral vector by injecting the at least one therapeutically effective amount of the rAAV viral vector into the right vagus nerve of the subject. The present disclosure provides at least one therapeutically effective amount of an rAAV viral vector for use in the treatment of a disease and/or disorder in the subject, wherein the at least one therapeutically effective amount of the rAAV viral vector is for administration to the subject via injection into the right vagus nerve of the subject. The present disclosure also provides the use of at least one therapeutically effective amount of an rAAV viral vector for the manufacture of a medicament for the treatment of a disease and/or disorder in a subject, wherein the at least one therapeutically effective amount of the rAAV viral vector is for administration to the subject via injection into the left vagus nerve of the subject.

The present disclosure provides a method of alleviating at least one symptom of autonomic dysfunction in a subject comprising administering at least one therapeutically effective amount of a gene therapy (e.g. an rAAV viral vector) into a vagus nerve of the subject.

The present disclosure provides a method of alleviating at least one symptom of autonomic dysfunction in a subject comprising administering at least one therapeutically effective amount of an rAAV viral vector into a vagus nerve of the subject. The present disclosure also provides at least one therapeutically effective amount of an rAAV vector for use in a method of alleviating at least one symptom of autonomic dysfunction in a subject, wherein the at least one therapeutically effective amount of the rAAV viral vector is for administration to the subject via injection into a vagus nerve of the subject. The present disclosure also provides the use of at least one therapeutically effective amount of an rAAV viral vector for the manufacture of a medicament for alleviating at least one symptom of autonomic dysfunction in a subject, wherein the at least one therapeutically effective amount of the rAAV viral vector is for administration to the subject via injection into a vagus nerve of the subject. In some aspects, a vagus nerve is the left vagus nerve. In some aspects, a vagus nerve is the right vagus nerve.

Symptoms of autonomic dysfunction can include, but are not limited to, dysarthria (difficulties in vocalization), dysphagia (difficulties in swallowing), problems with control of gastrointestinal tract motility (causing, e.g., loss of appetite, bloating, diarrhea, constipation), problems with control of blood pressure, and respiratory difficulties, orthostatic hypotension (resulting in dizziness and fainting), exercise intolerance (an inability to alter heart rate with exercise), sweating abnormalities (sweating too much and/or not sweating enough), urinary problems (e.g., difficulty starting urination, incontinence, and incomplete emptying of the bladder), and sexual problems (e.g., difficulty with ejaculation or maintaining an erection, vaginal dryness or difficulty having an orgasm). In some aspects an autonomic dysfunction can be related to a specific disease and/or disorder, including, but not limited to, neurological disorders.

The present disclosure provides a method of targeting a gene therapy (e.g. an rAAV viral vector) to the autonomic nervous system of a subject, the method comprising injecting at least one therapeutically effective amount of the gene therapy into a vagus nerve of the subject.

The present disclosure provides a method of targeting an rAAV viral vector to the autonomic nervous system of a subject, the method comprising injecting at least one therapeutically effective amount of the rAAV viral vector into a vagus nerve of the subject. The present disclosure also provides at least one therapeutically effective amount of an rAAV viral vector for use in a method of targeting the rAAV viral vector to the autonomic nervous system of the subject, wherein the at least one therapeutically effective amount of the rAAV is for administration of the subject via injection into a vagus nerve of the subject. The present disclosure also provides the use of at least one therapeutically effective amount of an rAAV viral vector for the manufacture of a medicament for targeting the rAAV viral vector to the autonomic nervous system of the subject, wherein the at least one therapeutically effective amount of the rAAV viral vector is for administration to the subject via injection into a vagus nerve of the subject. In some aspects, a vagus nerve is the left vagus nerve. In some aspects, a vagus nerve is the right vagus nerve.

The present disclosure provides a method of expressing an exogenous nucleic acid in the autonomic nervous system of a subject, the method comprising administering to the subject a composition comprising the exogenous nucleic via injection into a vagus nerve of the subject. The present disclosure provides a composition comprising an exogenous nucleic acid for use in a method for expressing the exogenous nucleic acid in the autonomic nervous system of a subject, wherein the composition is for administration to the subject via injection into a vagus nerve of the subject. The present disclosure provides the use of a composition comprising an exogenous nucleic acid in the manufacture of a medicament for a method of expressing the exogenous nucleic acid in the autonomic nervous system of a subject, wherein the composition is for administration to the subject via injection into a vagus nerve of the subject. In some aspects, a vagus nerve is the left vagus nerve. In some aspects, a vagus nerve is the right vagus nerve.

In some aspects, a composition comprising an exogenous nucleic acid can be a composition comprising the exogenous nucleic acid under transcriptional control and operatively linked to a promoter sequence. In some aspects, a composition comprising an exogenous nucleic acid can be an rAAV viral vector comprising the exogenous nucleic acid and/or the exogenous nucleic acid under transcriptional control and operatively linked to a promoter sequence.

The present disclosure provides a method of expressing an exogenous polypeptide in the autonomic nervous system of a subject, the method comprising administering to the subject a composition comprising a nucleic acid encoding the exogenous polypeptide via injection into a vagus nerve of the subject. The present disclosure provides a composition comprising a nucleic acid encoding an exogenous polypeptide for use in a method of expressing the exogenous polypeptide in the autonomic nervous system of the system, wherein the composition is for administration to the subject via injection into a vagus nerve of the subject. The present disclosure provides the use of a composition comprising a nucleic acid encoding an exogenous polypeptide for use in the manufacture of a medicament for use in a method of expressing the exogenous polypeptide in the autonomic nervous system of the subject, wherein the composition is for administration to the subject via injection into a vagus nerve of the subject. In some aspects, a vagus nerve is the left vagus nerve. In some aspects, a vagus nerve is the right vagus nerve.

In some aspects, a composition comprising a nucleic acid encoding an exogenous polypeptide can be a composition comprising the nucleic acid encoding the exogenous polypeptide under transcriptional control and operatively linked to a promoter sequence.

In some aspects, a composition comprising a nucleic acid encoding an exogenous polypeptide can be an rAAV viral vector comprising the nucleic acid encoding the exogenous polypeptide under transcriptional control and operatively linked to a promoter sequence.

Expression of an exogenous nucleic acid and/or polypeptide can include expression of the exogenous nucleic acid and/or polypeptide in a specific region of the autonomic nervous system. Non-limiting examples of specific regions of the autonomic nervous system include the area postrema, dorsal motor nucleus, sensory neurons of the autonomic nervous system, motor neurons of the autonomic nervous system, nodose ganglia, dorsal motor nucleus of the vagus, vagal circuits, nucleus *ambiguus*, or any other part of the autonomic nervous system known in the art.

In some aspects of the methods and uses of the present disclosure, a subject can be a subject that has been previously administered at least one amount of a gene therapy. Accordingly, the present disclosure provides a method of treating a disease and/or disorder in a subject comprising administering to the subject at least one therapeutically effective amount of a gene therapy by injecting the at least one therapeutically effective amount of the gene therapy into a vagus nerve of the subject, wherein the subject has been previously administered an initial gene therapy. In some aspects, the gene therapy administered via a vagus nerve of the subject can be a different gene therapy than the initial gene therapy. In some aspects, the gene therapy administered via a vagus nerve of the subject can be the same gene therapy as the initial gene therapy. In some aspects, the initial gene therapy can have been administered via an administration route that is not the vagus nerve. In some aspects, the initial gene therapy can have been administered intravenously, intrathecally, intracerebrally, intraventricularly, intranasally, intratracheally, intra-aurally, intra-ocularly, or peri-ocularly, orally, rectally, transmucosally, inhalationally, transdermally, parenterally, subcutaneously, intradermally, intramuscularly, intracisternally, intranervally, intrapleurally, topically, intralymphatically, intracisternally or intranerve. In some aspects, the initial gene therapy can have been administered intrathecally.

In some aspects of the methods and uses of the present disclosure, a subject can be a subject has been previously administered at least one amount of an initial rAAV viral vector. Accordingly, the present disclosure provides a method of treating a disease and/or disorder in a subject comprising administering to the subject at least one therapeutically effective amount of an rAAV viral vector by injecting the at least one therapeutically effective amount of the rAAV viral vector into a vagus nerve of the subject, wherein the subject has been previously administered an initial rAAV viral vector. In some aspects, the rAAV viral vector administered via a vagus nerve of the subject can be a different rAAV viral vector than the initial rAAV viral vector. In some aspects, the rAAV viral vector administered via the vagus nerve of the subject can be the same as the initial rAAV viral vector. In some aspects, the rAAV viral vector administered via a vagus nerve of the subject can comprise a first AAV capsid protein and the initial rAAV viral vector can comprise a second AAV capsid protein, wherein the first AAV capsid protein is a different serotype as the second AAV capsid protein. In some aspects, the rAAV viral vector administered via a vagus nerve of the subject can comprise a first AAV capsid protein and the initial rAAV viral vector can comprise a second AAV capsid protein, wherein the first AAV capsid protein is the same serotype as the second AAV capsid protein (e.g., an AAV9 capsid protein). In some aspects, the initial rAAV viral vector can have been administered via an administration route that is not the vagus nerve. In some aspects, the initial rAAV viral vector can have been administered intravenously, intrathecally, intracerebrally, intraventricularly, intranasally, intratracheally, intra-aurally, intra-ocularly, or peri-ocularly, orally, rectally, transmucosally, inhalationally, transdermally, parenterally, subcutaneously, intradermally, intramuscularly, intracisternally, intranervally, intrapleurally, topically, intralymphatically, intracisternally or intranerve. In some aspects, the initial rAAV viral vector can have been administered intrathecally.

In some aspects of the methods and uses of the present disclosure, a subject can be a subject that is seropositive for the gene therapy that is to be administered via injection into a vagus nerve. Accordingly, the present disclosure provides a method of treating a disease and/or disorder in a subject comprising administering at least one therapeutically effective amount of a gene therapy to the subject by injecting the at least one therapeutically effective amount of the gene therapy into a vagus nerve of the subject, wherein the subject is seropositive for the gene therapy.

In some aspects of the methods and uses of the present disclosure, a subject can be a subject that is seropositive for an AAV particle that is the same serotype as the rAAV viral vector that is to be administered via injection into a vagus nerve. Accordingly, the present disclosure provides a method of treating a disease and/or disorder in a subject comprising administering to the subject at least one therapeutically effective amount of an rAAV viral vector by injecting the at least one therapeutically effective amount of the gene therapy into a vagus nerve of the subject, wherein the subject is seropositive for an AAV particle that is the same serotype as the rAAV viral vector that is to be administered via injection into a vagus nerve.

As used herein, the term "seropositive" refers to the presence of a serological marker in the blood of a subject. Thus, in a non-limiting example, a subject who is said to be seropositive for an AAV viral vectors comprising an AAV9 capsid is a subject who has AAV viral vectors comprising an AAV9 capsid in their blood. In another non-limiting example, a subject who is said to be seropositive for a neutralizing antibody is a subject who has a neutralizing antibody in their blood.

In some aspects of the methods and uses of the present disclosure, a subject can be a subject that has neutralizing antibodies against the gene therapy that is to be administered via injection into a vagus nerve. Accordingly, the present disclosure provides a method of treating a disease and/or disorder in a subject comprising administering at least one therapeutically effective amount of a gene therapy to the subject by injecting the at least one therapeutically effective amount of the gene therapy into a vagus nerve of the subject, wherein the subject has neutralizing antibodies against the gene therapy.

In some aspects of the methods and uses of the present disclosure, a subject can be a subject that has neutralizing antibodies against an AAV particle with the same serotype as the rAAV viral vector that is to be administered via injection into a vagus nerve. Accordingly, the present disclosure provides a method of treating a disease and/or disorder in a subject comprising administering at least one therapeutically effective amount of an rAAV viral vector by injecting the at least one therapeutically effective amount of the rAAV viral vector into a vagus nerve, wherein the subject has neutralizing antibodies against an AAV particle with the same serotype as the rAAV viral vector. In a non-limiting example, the present disclosure provides a method of treating a disease and/or disorder in a subject comprising administering at least one therapeutically effect amount of an rAAV viral vector by injecting the at least one therapeutically effective amount of the rAAV viral vector into a vagus nerve, wherein the rAAV viral vector comprises an AAV9 capsid protein, wherein the subject has neutralizing antibodies against an AAV particle comprising an AAV9 capsid.

The presence of neutralizing antibodies against a gene therapy or an AAV particle with particular serotype can be determined using methods standard in the art and well-known to the skilled artisan.

The present disclosure provides a method of treating a disease and/or disorder in a subject comprising administering: a) at least one therapeutically effective amount of a first gene therapy; and b) at least one therapeutically effective amount of a second gene therapy, wherein the at least one therapeutically effective amount of the second gene therapy is administered via injection into a vagus nerve of the subject. The present disclosure provides at least one therapeutically effective amount of a first gene therapy and at least one therapeutically effective amount of a second gene therapy for use in the treatment of a disease and/or disorder in a subject, wherein the at least one therapeutically effective amount of the second gene therapy is for administration to the subject via injection into a vagus nerve of the subject. The present disclosure provide the use of at least one therapeutically effective amount of a first gene therapy and at least one therapeutically effective amount of a second gene therapy for the manufacture of a medicament for the treatment of a disease and/or disorder in a subject, wherein the at least one therapeutically effective amount of the second gene therapy is for administration to the subject via injection into a vagus nerve of the subject. In some aspects, a vagus nerve can be the left vagus nerve. In some aspects, a vagus nerve can be the right vagus nerve.

In some aspects of the preceding methods and uses, the first gene therapy and the second gene therapy can be the same. In some aspects of the preceding methods and uses, the first gene therapy and the second gene therapy can be different.

In some aspects of the preceding method, the first gene therapy can be administered to the subject via an administration route that is not injection into a vagus nerve of the subject. In some aspects, the first gene therapy is administered intravenously, intrathecally, intracerebrally, intraventricularly, intranasally, intratracheally, intra-aurally, intraocularly, or peri-ocularly, orally, rectally, transmucosally, inhalationally, transdermally, parenterally, subcutaneously, intradermally, intramuscularly, intracisternally, intranervally, intrapleurally, topically, intralymphatically, intracisternally or intranerve. Accordingly, in a non-limiting example, the present disclosure provides a method of treating a disease and/or disorder in a subject comprising administering: a) at least one therapeutically effective amount of a first gene therapy, wherein the at least one therapeutically effective amount of the first gene therapy is administered to the subject intrathecally; and b) at least one therapeutically effective amount of a second gene therapy, wherein the at least one therapeutically effective amount of the second gene therapy is administered to the subject via injection into a vagus nerve of the subject.

The present disclosure provides a method of treating a disease and/or disorder in a subject comprising administering: a) at least one therapeutically effective amount of a first rAAV viral vector; and b) at least one therapeutically effective amount of a second rAAV viral vector, wherein the at least one therapeutically effective amount of the second rAAV viral vector is administered via injection into a vagus nerve of the subject. The present disclosure also provides at least one therapeutically effective amount of a first rAAV viral vector and at least one therapeutically effective amount of a second rAAV viral vector for use in the treatment of a disease and/or disorder in a subject, wherein the at least one therapeutically effective amount of the second rAAV viral vector is for administration to the subject via injection into a vagus nerve of the subject. The present disclosure also provides the use of at least one therapeutically effective amount of a first rAAV viral vector and at least one therapeutically effective amount of a second rAAV viral vector in the manufacture of a medicament for the treatment of a disease and/or disorder in a subject, wherein the at least one therapeutically effective amount of the second rAAV viral vector is for administration to the subject via injection into a vagus nerve of the subject. In some aspects, a vagus nerve can be the left vagus nerve. In some aspects, a vagus nerve can be the right vagus nerve.

In some aspects of the preceding method, the first rAAV viral vector and the second rAAV viral vector can be the same. In some aspects of the preceding method, the first rAAV viral vector and the second rAAV viral vector can be different.

In some aspects of the preceding method, the first rAAV viral vector and the second rAAV viral vector can be the same serotype. Accordingly, in a non-limiting example, the first rAAV viral vector comprises an AAV9 capsid protein and the second rAAV viral vector comprises an AAV9 capsid protein.

In some aspects of the preceding method, the first rAAV viral vector is administered to the subject via an administration route that is not injection into a vagus nerve of the subject. In some aspects, the first rAAV viral vector is administered intravenously, intrathecally, intracerebrally, intraventricularly, intranasally, intratracheally, intra-aurally, intra-ocularly, or peri-ocularly, orally, rectally, transmucosally, inhalationally, transdermally, parenterally, subcutaneously, intradermally, intramuscularly, intracisternally, intranervally, intrapleurally, topically, intralymphatically, intracisternally or intranerve. Accordingly, in a non-limiting example, the present disclosure provides a method of treating a disease and/or disorder in a subject comprising administering: a) at least one therapeutically effective amount of a first rAAV viral vector, wherein the at least one therapeutically effective amount of the first rAAV viral vector is administered to the subject intrathecally; and b) at least one therapeutically effective amount of a second rAAV viral vector, wherein the at least one therapeutically effective amount of the second rAAV viral vector is administered to the subject via injection into a vagus nerve of the subject.

In some aspects of the methods and uses of the present disclosure wherein a subject is administered a first gene therapy and a second gene therapy (e.g., a first rAAV viral vector and a second rAAV viral vector), the first gene therapy and the second gene therapy can be administered in temporal proximity.

As used herein, the term "temporal proximity" refers to that administration of one therapeutic composition (e.g., a first gene therapy) occurs within a time period before or after the administration of another therapeutic composition (e.g., a second gene therapy), such that the therapeutic effect of the one therapeutic agent overlaps with the therapeutic effect of the other therapeutic agent. In some embodiments, the therapeutic effect of the one therapeutic agent completely overlaps with the therapeutic effect of the other therapeutic agent. In some embodiments, "temporal proximity" means that administration of one therapeutic agent occurs within a time period before or after the administration of another therapeutic agent, such that there is a synergistic effect between the one therapeutic agent and the other therapeutic agent. "Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, "temporal proximity" means within 1 month, within 2 months, within 3 months, within 4 months, within 5 months, within 6 months, within 7 months, within 8 months, within 9 months, within 10 months, within 11 months or within 12 months. In some embodiments, "temporal proximity" means within 1 year, within 2 years, within 3 years, within 4 years, within 5 years, within 6 years, within 7 years, within 8 years, within 9 years or within 10 years. In some embodiments, multiple administration of one therapeutic agent can occur in temporal proximity to a single administration of another therapeutic agent. In some embodiments, temporal proximity may change during a treatment cycle or within a dosing regimen.

In some aspects of the methods and uses of the present disclosure wherein a subject is administered a first gene therapy and a second gene therapy (e.g., a first rAAV viral vector and a second rAAV viral vector), the first gene therapy and the second gene therapy can be administered concurrently.

In some aspects of the methods and uses of the present disclosure wherein a subject is administered a first gene therapy and a second gene therapy (e.g., a first rAAV viral vector and a second rAAV viral vector), the first gene therapy and the second gene therapy can be administered sequentially.

In some aspects of the methods and uses of the present disclosure, a gene therapy can be a gene therapy that is designed, according with standard methods that are well-known to one of ordinary skill in the art, to treat at least one or more of Spinal muscular atrophy, Friedrich's ataxia, CLN3 Batten, CLN6 Batten, CLN7 Batten, Epileptic encephalopathy, Leigh Syndrome, Charcot Marie Tooth disease, Giant axonal neuropathy, Lafora disease, SLC13A5 Epileptic Encephalopathy, Congenital Disorder of Glycosylation, Type Iq, Kahrizi Syndrome, Angelman Syndrome, Rett Syndrome, Spastic paraplegia, Alternating hemiplegia of childhood and Zellweger spectrum disorders. In a non-limiting example, and as would be appreciated by the skilled artisan, the gene therapy can be a gene therapy that is designed to deliver a nucleic acid encoding for a therapeutic protein, wherein the expression of the therapeutic protein results in the treatment of the disease and/or disorder. In another non-limiting example, and as would be appreciated by the skilled artisan, the gene therapy can be a gene therapy that is designed to deliver a regulatory nucleic acid (e.g. a siRNA, an miRNA, a anti-sense oligonucleotide, a shRNA, etc.) that upregulates or downregulates the expression and/or activity of an endogenous nucleic acid and/or protein.

Non-limiting examples of gene therapy include viral-based gene therapies (e.g., lentiviral vectors, AAV vectors, adenoviral vectors, etc.), non-viral gene therapy (e.g., linear oligonucleotides, circular plasmids, human artificial chromosomes), CRISPR-based gene therapy, antisense oligonucleotide-based gene therapy, nanoparticle-mediated gene therapy or any other gene therapy known in the art. A gene therapy can comprise a viral vector (e.g. an rAAV viral vector), a plasmid, a bacteriophage, bacterial chromosomes, artificial chromosomes, a transposon or any combination thereof.

A gene therapy can comprise a gene expression cassette. Expression cassettes can be a circular or linear nucleic acid molecule. In some cases, an expression cassette is delivered to cells (e.g., a plurality of different cells or cell types including target cells or cell types and/or non-target cell types) in a vector (e.g., an expression vector). Gene expression cassettes can be designed to drive expression of a gene, such as a codon-optimized gene. Examples of genes are shown in Table 1. Expression cassettes can be used for research and to test gene replacement strategies for genetic disorders shown in, for example Table 1. Expression cassettes can also be used to treat disorders, diseases, or conditions resulting from these gene deficiencies.

A gene expression cassette can express a functional gene in cells receiving the cassette. An expression cassette can include, for example, a promoter for strong, medium, or low expression. An expression cassette can include a ubiquitous promoter for expression in many or all tissues. Any tissue-specific promoter can be included in expression cassettes provided herein. A gene included in expression cassettes provided herein can be codon-optimized to facilitate optimal gene expression. Thus, a sequence of a gene can be non-naturally occurring.

Provided herein, in some embodiments, are expression cassettes comprising a polynucleotide encoding a gene associated with a neurological disorder (see, e.g., Table 1). Polynucleotides encoding a gene can comprise (I) a polynucleotide set forth in, for example, Table 1, or (II) a polynucleotide having at least 85% identity, at least 90% identity, at least 95% identity, at least 96% identity, at least 97% identity, at least 98% identity, at least 99% identity, at least 99.5% identity, at least 99.9% identity, and any number or range in between, to a gene shown in Table 1. In an embodiment, a gene included in expression cassettes provided herein is a human gene. A gene included in expression cassettes provided herein can be codon-optimized.

Expression cassettes provided herein can further comprise a promoter driving expression of a gene. Any promoter can be used, including ubiquitous, constitutive, inducible, and tissue-specific promoters, for example. Promoters from any species can be used, including human, ape, monkey, mouse, rat, chicken, and others. In an embodiment, the promoter driving expression of a gene is a strong, ubiquitous promoter. In an embodiment, the promoter driving expression of a gene is a promoter that can provide for neuron-specific expression.

Additional regulatory elements and other elements that can influence gene expression can be included in expression cassettes provided herein, such as Kozak consensus sequences, poly(A) signals, 5' and 3' inverted terminal repeats (ITRs) of adeno-associated virus (AAV), for example, and others.

Inverted terminal repeat (ITR) sequences of AAV are symmetrical sequences of about 145 bases each. AAV ITRs are located at the 5' and 3' end of the viral genome. ITRs are important for efficient AAV genome multiplication. ITR sequences can flank a heterologous polynucleotide, i.e., a polynucleotide that is not of AAV origin, in an AAV vector, for example.

A mutated ITR can be included in the expression cassettes provided herein. The 5' ITR and/or the 3' ITR can be mutated. In an embodiment, the 5' ITR is mutated. In an embodiment, the 3' ITR is mutated. In an embodiment, the 5' ITR and the 3' ITR are mutated. An ITR can be mutated to be self-complementary. In an embodiment, the 3' ITR is mutated for self-complementarity.

In some aspects of the methods and uses of the present disclosure, the vagus nerve is the left vagus nerve. In some aspects of the methods and uses of the present disclosure, the vagus nerve is the right vagus nerve.

In some aspects of the methods and uses of the present disclosure, an rAAV viral vector can be any of the rAAV viral vectors described herein, including, but not limited to, rAAV viral vectors comprising nucleic acid sequences encoding a GAN polypeptide.

In some aspects, the disease and/or disorder can be a genetic disorder involving the GAN gene. A genetic disorder involving the GAN gene can be GAN loss, misfunction and/or deficiency.

In some aspects, the disease can be a disorder involving the GAN protein. A genetic disorder involving the GAN protein can be GAN loss, misfunction and/or deficiency.

A disease and/or disorder can be Giant Axonal Neuropathy.

In some aspects, a disease and/or disorder can be a disease and/or disorder that is characterized by the loss-of-function of at least one copy of the GAN gene in the genome of a subject. In some aspects, a disease and/or disorder can be a disease and/or disorder that is characterized by a decrease in function of at least one copy of the GAN gene in the genome of a subject. In some aspects, a disease and/or disorder can be a disease and/or disorder that is characterized by at least one mutation in at least one mutation in at least one copy of the GAN gene in the genome of the subject.

A subject in the methods provided herein can be deficient in GAN and/or GAN. As used herein, "GAN deficiency" means that a subject can have one or more mutations in the GAN gene or lacks a functional GAN gene. As used herein, "GAN deficiency" means that a subject can have one or more mutations in the GAN protein or lacks a functional GAN protein.

A mutation in a GAN gene or GAN protein can be any type of mutation that is known in the art. Non-limiting examples of mutations include somatic mutations, single nucleotide variants (SNVs), nonsense mutations, insertions, deletions, duplications, frameshift mutations, repeat expansions, short insertions and deletions (INDELs), long INDELs, alternative splicing, the products of alternative splicing, altered initiation of translation, the products of altered initiation of translation, proteomic cleavage, the products of proteomic cleavage.

In some aspects, a disease and/or disorder can be a disease and/or disorder that is characterized by a decrease in expression of the GAN gene in a subject as compared to a control subject that does not have the disease and/or disorder. In some aspects, the decrease in expression can be at least about 10%, or at least about 20%, or at least about 30%, or at least about 40%, or at least about 50%, or at least about 60%, or at least about 70%, or at least about 80%, or at least about 90%, or at least about 95%, or at least about 99%, or at least about 100%.

In some aspects, a disease and/or disorder can be a disease and/or disorder that is characterized by a decrease in the amount of GAN protein in a subject as compared to a control subject that does not have the disease and/or disorder. In some aspects, the decrease in the amount of GAN protein can be at least about 10%, or at least about 20%, or at least about 30%, or at least about 40%, or at least about 50%, or at least about 60%, or at least about 70%, or at least about 80%, or at least about 90%, or at least about 95%, or at least about 99%, or at least about 100%.

In some aspects, a disease and/or disorder can be a disease and/or disorder that is characterized by a decrease in the activity of GAN protein in a subject as compared to a control subject that does not have the disease and/or disorder. In some aspects, the decrease in the activity of GAN protein can be at least about 10%, or at least about 20%, or at least about 30%, or at least about 40%, or at least about 50%, or at least about 60%, or at least about 70%, or at least about 80%, or at least about 90%, or at least about 95%, or at least about 99%, or at least about 100%.

In some aspects of the methods and uses of the present disclosure, the disease and/or disorder can be a disorder of the nervous system.

In some aspects of the methods and uses of the present disclosure, the disease and/or disorder can be one or more of Spinal muscular atrophy, Friedrich's ataxia, CLN3 Batten, CLN6 Batten, CLN7 Batten, Epileptic encephalopathy, Leigh Syndrome, Charcot Marie Tooth disease, Giant axonal neuropathy, Lafora disease, SLC13A5 Epileptic Encephalopathy, Congenital Disorder of Glycosylation, Type Iq, Kahrizi Syndrome, Angelman Syndrome, Rett Syndrome, Spastic paraplegia, Alternating hemiplegia of childhood and Zellweger spectrum disorders. Exemplary nervous system disorders including exemplary genes and polynucleotides associated with the disorders are shown in Table 1 below. These exemplary genes and polynucleotides encode therapeutic polypeptides associated with one or more nervous system disorders.

TABLE 1

| Disease | Gene | Protein | Exemplary NCBI Ref. Seq. |
|---|---|---|---|
| Spinal muscular atrophy | SMN1 | Survival motor neuron gene 1 | NG_008691.1 |
| Friedrich's ataxia | FXN | Frataxin | NG_008845.2 |
| CLN3 Batten | CLN3 | CLN3 | NG_008654.2 |
| CLN6 Batten | CLN6 | CLN6 | NG_008764.2 |
| CLN7 Batten | CLN7 | CLN7 | NG_008657.1 |
| Epileptic encephalopathy | SLC6A1 | Solute carrier family 6 member 1 | NG_053003.1 |
| Leigh Syndrome | SURF1 | Surfeit locus protein 1 | NG_008477.1 |
| Charcot Marie Tooth disease | MFN2 | Mitofusin 2 | NG_007945.1 |
| Giant axonal neuropathy | GAN | Gigaxonin | NG_009007.1 |
| Lafora disease | EPM2A | Laforin | NG_012832.2 |
|  | NHLRC1 | Malin | NG_016750.1 |
| SLC13A5 Epileptic Encephalopathy | SLC13A5 | Sodium dependent citrate transporter | NG_034220.1 |
| Congenital Disorder of Glycosylation, Type Iq, Kahrizi Syndrome | SRD5A3 | Steroid 5 α-reductase 3 | NG_028230.1 |
| Angelman Syndrome | UBE3A | E3 Ubiquitin Ligase | NG_009268.1 |
| Rett Syndrome | MECP2 | Methyl-CpG binding protein 2 | NG_007107.2 |
| Spastic paraplegia | SPG7 | Paraplegin | NG_008082.1 |
| Alternating hemiplegia of childhood | ATP1A3 | α subunit of Na+/K+ APTase | NG_008015.1 |
|  | ATP1A2 |  | NG_008014.1 |
| Zellweger spectrum disorders | PEX1 | Peroxisomal biogenesis factor 1 | NG_008341.2 |
|  | PEX2 | Peroxisomal biogenesis factor 2 | NG_008371.1 |
|  | PEX3 | Peroxisomal biogenesis factor 3 | NG_008459.1 |
|  | PEX5 | Peroxisomal biogenesis factor 5 | NG_008448.1 |
|  | PEX6 | Peroxisomal biogenesis factor 6 | NG_008370.1 |
|  | PEX7 | Peroxisomal biogenesis factor 7 | NG_008462.1 |
|  | PEX10 | Peroxisomal biogenesis factor 10 | NG_008342.1 |
|  | PEX11β | Peroxisomal biogenesis factor 11β | NG_033000.3 |
|  | PEX12 | Peroxisomal biogenesis factor 12 | NG_008447.1 |
|  | PEX13 | Peroxisomal biogenesis factor 13 | NG_008665.1 |
|  | PEX14 | Peroxisomal biogenesis factor 14 | NG_008340.2 |
|  | PEX16 | Peroxisomal biogenesis factor 16 | NG_008460.1 |
|  | PEX19 | Peroxisomal biogenesis factor 19 | NG_008637.1 |
|  | PEX26 | Peroxisomal biogenesis factor 26 | NG_008339.1 |
| Creatine transport disorders | SLC6A8 | Sodium- and chloride-dependent creatine transporter 1; | NG_012016.2 |
| GNAO1 encephalopathy | GNAO1 | G Protein subunit alpha o1 | NG_042800.1 |
| Parkinson's disease | GDNF | Glial cell line derived neurotropic factor | NG_011675.2 |
|  | DCC | Netrin 1 receptor | NG_013341.2 |
|  | NRTN | Neurturin | NG_008202.1 |
| Unverricht-Lundborg Disease | CSTB | Cystatin B | NG_011545.1 |
| Adult polyglucosan body disease | GBE1 | Glycogen branching enzyme | NG_011810.1 |

In some aspects, a subject can be less than 0.5 years of age, or less than 1 year of age, or less than 1.5 years of age, or less than 2 years of age, or at less than 2.5 years of age, or less than 3 years of age, or less than 3.5 years of age, or less than 3.5 years of age, or less than 4 years of age, or less than 4.5 years of age, or less than 5 years of age, or less than 5.5 years of age, or less than 6 years of age, or less than 6.5 years of age, or less than 7 years of age, or less than 7.5 years of age, or less than 8 years of age, or less than 8.5 years of age, or less than 9 years of age, or less than 9.5 years of age, or less than 10 years of age. In some aspects the subject can be less than 11 years of age, less than 12 years of age, less than 13 years of age, less than 14 years of age, less than 15 years of age, less than 20 years of age, less than 30 years of age, less than 40 years of age, less than 50 years of age, less than 60 years of age, less than 70 years of age, less than 80 years of age, less than 90 years of age, less than 100 years of age, less than 110 years of age, or less than 120 years of age. In some aspects, a subject can be less than 0.5 years of age. In some aspects, a subject can be less than 4 years of age. In some aspects, a subject can be less than 10 years of age.

The methods of treatment and prevention disclosed herein may be combined with appropriate diagnostic techniques to identify and select patients for the therapy or prevention.

The disclosure provides methods of increasing the level of a protein in a host cell, comprising contacting the host cell with any one of the rAAV viral vectors disclosed herein, wherein the rAAV viral vectors comprises any one of the rAAV vectors disclosed herein, comprising a transgene nucleic acid molecule encoding the protein. In some aspects, the protein is a therapeutic protein. In some aspects, the host cell is in vitro, in vivo, or ex vivo. In some aspects, the host cell is derived from a subject. In some aspects, the subject suffers from a disorder, which results in a reduced level and/or functionality of the protein, as compared to the level and/or functionality of the protein in a normal subject.

In some aspects, the level of the protein is increased to level of about $1 \times 10^{-7}$ ng, about $3 \times 10^{-7}$ ng, about $5 \times 10^{-7}$ ng, about $7 \times 10^{-7}$ ng, about $9 \times 10^{-7}$ ng, about $1 \times 10^{-6}$ ng, about $2 \times 10^{-6}$ ng, about $3 \times 10^{-6}$ ng, about $4 \times 10^{-6}$ ng, about $6 \times 10^{-6}$ ng, about $7 \times 10^{-6}$ ng, about $8 \times 10^{-6}$ ng, about $9 \times 10^{-6}$ ng, about $10 \times 10^{-6}$ ng, about $12 \times 10^{-6}$ ng, about $14 \times 10^{-6}$ ng, about $16 \times 10^{-6}$ ng, about $18 \times 10^{-6}$ ng, about $20 \times 10^{-6}$ ng, about $25 \times 10^{-6}$ ng, about $30 \times 10^{-6}$ ng, about $35 \times 10^{-6}$ ng, about $40 \times 10^{-6}$ ng, about $45 \times 10^{-6}$ ng, about $50 \times 10^{-6}$ ng, about $55 \times 10^{-6}$ ng, about $60 \times 10^{-6}$ ng, about $65 \times 10^{-6}$ ng, about $70 \times 10^{-6}$ ng, about $75 \times 10^{-6}$ ng, about $80 \times 10^{-6}$ ng, about $85 \times 10^{-6}$ ng, about $90 \times 10^{-6}$ ng, about $95 \times 10^{-6}$ ng, about $10 \times 10^{-5}$ ng, about $20 \times 10^{-5}$ ng, about $30 \times 10^{-5}$ ng, about $40 \times 10^{-5}$ ng, about $50 \times 10^{-5}$ ng, about $60 \times 10^{-5}$ ng, about $70 \times 10^{-5}$ ng, about $80 \times 10^{-5}$ ng, or about $90 \times 10^{-5}$ ng in the host cell.

The disclosure provides methods of introducing a gene of interest to a cell in a subject comprising contacting the cell with an effective amount of any one of the rAAV viral vectors disclosed herein, wherein the rAAV viral vectors contain any one of the rAAV vectors disclosed herein, comprising the gene of interest.

In some aspects of the methods of the present disclosure, a subject can also be administered a prophylactic immunosuppressant treatment regimen in addition to being administered an rAAV vector or rAAV viral vector of the present disclosure. In some aspects, an immunosuppressant treatment regimen can comprise administering at least one immunosuppressive therapeutic. Non limiting examples of immunosuppressive therapeutics include, but are not limited to, Sirolimus (rapamycin), acetaminophen, diphenhydramine, IV methylprednisolone, prednisone, or any combination thereof. An immunosuppressive therapeutic can be administered prior to the day of administration of the rAAV vector and/or rAAV viral vector, on the same day as the administration of the rAAV vector and/or rAAV viral vector, or any day following the administration of the rAAV vector and/or rAAV viral vector.

A "subject" of diagnosis or treatment is a cell or an animal such as a mammal, or a human. A subject is not limited to a specific species and includes non-human animals subject to diagnosis or treatment and those subject to infections or animal models, including, without limitation, simian, murine, rat, canine, or leporid species, as well as other livestock, sport animals, or pets. In some aspects, the subject is a human.

As used herein, "treating" or "treatment" of a disease in a subject refers to (1) inhibiting the disease or arresting its development; or (2) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

As used herein, "preventing" or "prevention" of a disease refers to preventing the symptoms or disease from occurring in a subject that is predisposed or does not yet display symptoms of the disease.

As used herein the term "effective amount" and/or "therapeutically effective amount" intends to mean a quantity sufficient to achieve a desired effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of gene therapy, the effective amount can be the amount sufficient to result in regaining part or full function of a gene that is deficient in a subject. In some aspects, the effective amount of an rAAV viral vector is the amount sufficient to result in expression of a gene in a subject such that a GAN polypeptide is produced. In some aspects, the effective amount is the amount required to increase galactose metabolism in a subject in need thereof. The skilled artisan will be able to determine appropriate amounts depending on these and other factors.

In some aspects, the effective amount will depend on the size and nature of the application in question. It will also depend on the nature and sensitivity of the target subject and the methods in use. The skilled artisan will be able to determine the effective amount based on these and other considerations. The effective amount may comprise, consist essentially of, or consist of one or more administrations of a composition depending on the embodiment.

As used herein, the term "administer" or "administration" intends to mean delivery of a substance to a subject such as an animal or human. Administration can be effected in one dose, continuously or intermittently throughout the course of treatment. Methods of determining the most effective means and dosage of administration are known to those of skill in the art and will vary with the composition used for therapy, the purpose of the therapy, as well as the age, health or gender of the subject being treated. Single or multiple administrations can be carried out with the dose level and pattern being selected by the treating physician or in the case of pets and other animals, treating veterinarian.

Methods of determining the most effective means and dosage of administration are known to those of skill in the art and will vary with the composition used for therapy, the purpose of the therapy and the subject being treated. Single or multiple administrations can be carried out with the dose level and pattern being selected by the treating physician. It is noted that dosage may be impacted by the route of administration. Suitable dosage formulations and methods of administering the agents are known in the art. Non-limiting examples of such suitable dosages may be as low as $10^9$ vector genomes to as much as $10^{17}$ vector genomes per administration.

In some aspects of the methods described herein, the number of viral particles (e.g., rAAV viral vectors) administered to the subject ranges from about $10^9$ to about $10^{17}$. In some aspects, about $10^{10}$ to about $10^{12}$, about $10^{11}$ to about $10^{13}$, about $10^{11}$ to about $10^{12}$, about $10^{11}$ to about $10^{14}$, about $10^{12}$ to about $10^{16}$, about $10^{13}$ to about $10^{16}$, about $10^{14}$ to about $10^{15}$, about $5 \times 10^{11}$ to about $5 \times 10^{12}$, about $10^{11}$ to about $10^{18}$, about $10^{13}$ to about $10^{16}$, or about $10^{12}$ to about $10^{13}$ viral particles are administered to the subject.

In some aspects of the methods described herein, the number of viral particles (e.g., rAAV viral vectors) administered to the subject is at least about $10^{10}$, or at least about $10^{11}$, or at least about $10^{12}$, or at least about $10^{13}$, or at least about $10^{14}$, or at least about $10^{15}$, or at least about $10^{16}$, or at least about $10^{17}$ viral particles.

In some aspects of the methods described herein the number of viral particles (e.g. rAAV viral vectors) administered to the subject is about $3.5\times10^{13}$ viral particles. In some aspects of the methods described herein the number of viral particles (e.g. rAAV viral vectors) administered to the subject is about $3.5\times10^{14}$ viral particles. In some aspects of the methods described herein the number of viral particles (e.g. rAAV viral vectors) administered to the subject is about $3.5\times10^{13}$ to about $3.5\times10^{14}$ viral particles.

In some aspects of the methods described herein, the number of viral particles (e.g., rAAV viral vectors) administered to the subject can depend on the age of the subject. In non-limiting examples, a subject that is 7 years of age or older can be administered about $10\times10^{14}$ viral particles, a subject that is about 4 years of age to about 7 years of age can be administered about $10\times10^{14}$ viral particles, a subject that is about 3 years of age to about 4 years of age can be administered about $9\times10^{14}$ viral particles, a subject that is about 2 years of age to about 3 years of age can be about $8.2\times10^{14}$ viral particles, a subject that is about 1 year of age to about 2 years of age can be administered about $7.3\times10^{14}$ viral particles, a subject that is about 0.5 years of age to about 1 year of age can be administered about $4\times10^{14}$ viral particles, or a subject that is less than 0.5 years of age can be administered $3\times10^{14}$ viral particles.

In some aspects, the amounts of viral particles in a composition, pharmaceutical composition, or the amount of viral particles administered to a patient can calculated based on the percentage of viral particles that are predicted to contain viral genomes.

In some aspects, rAAV viral vectors of the present disclosure can be introduced to the subject intravenously, intrathecally, intracerebrally, intraventricularly, intranasally, intratracheally, intra-aurally, intra-ocularly, or peri-ocularly, orally, rectally, transmucosally, inhalationally, transdermally, parenterally, subcutaneously, intradermally, intramuscularly, intracisternally, intranervally, intrapleurally, topically, intralymphatically, intracisternally; such introduction may also be intra-arterial, intracardiac, subventricular, epidural, intracerebral, intracerebroventricular, sub-retinal, intravitreal, intraarticular, intraperitoneal, intrauterine, intranerve or any combination thereof. In some aspects, the viral particles are delivered to a desired target tissue, e.g., to the lung, eye, or CNS, as non-limiting examples. In some aspects, delivery of viral particles is systemic. The intracisternal route of administration involves administration of a drug directly into the cerebrospinal fluid of the brain ventricles. It could be performed by direct injection into the cisterna *magna* or via a permanently positioned tube. In some aspects, the rAAV viral vectors of the present disclosure are administered intrathecally.

In some aspects, the rAAV viral vectors of the present disclosure repair a gene deficiency in a subject. In some aspects, the ratio of repaired target polynucleotide or polypeptide to unrepaired target polynucleotide or polypeptide in a successfully treated cell, tissue, organ or subject is at least about 1.5:1, about 2:1, about 3:1, about 4:1, about 5:1, about 6:1, about 7:1, about 8:1, about 9:1, about 10:1, about 20:1, about 50:1, about 100:1, about 1000:1, about 10,000:1, about 100,000:1, or about 1,000,000:1. The amount or ratio of repaired target polynucleotide or polypeptide can be determined by any method known in the art, including but not limited to western blot, northern blot, Southern blot, PCR, sequencing, mass spectrometry, flow cytometry, immunohistochemistry, immunofluorescence, fluorescence in situ hybridization, next generation sequencing, immunoblot, and ELISA.

Administration of the rAAV vectors, rAAV viral vectors, compositions or pharmaceutical compositions of this disclosure can be effected in one dose, continuously or intermittently throughout the course of treatment. In some aspects, the rAAV vectors, rAAV viral vectors, compositions, or pharmaceutical compositions of this disclosure are parenterally administered by injection, infusion, or implantation.

In some aspects, the rAAV viral vectors of this disclosure show enhanced tropism for brain and cervical spine. In some aspects, the rAAV viral vectors of the disclosure can cross the blood-brain-barrier (BBB).

Methods of Manufacture

A variety of approaches may be used to produce rAAV viral vectors of the present disclosure. In some aspects, packaging is achieved by using a helper virus or helper plasmid and a cell line. The helper virus or helper plasmid contains elements and sequences that facilitate viral vector production. In another aspect, the helper plasmid is stably incorporated into the genome of a packaging cell line, such that the packaging cell line does not require additional transfection with a helper plasmid.

In some aspects, the cell is a packaging or helper cell line. In some aspects, the helper cell line is eukaryotic cell; for example, an HEK 293 cell or 293T cell. In some aspects, the helper cell is a yeast cell or an insect cell.

In some aspects, the cell comprises a nucleic acid encoding a tetracycline activator protein; and a promoter that regulates expression of the tetracycline activator protein. In some aspects, the promoter that regulates expression of the tetracycline activator protein is a constitutive promoter. In some aspects, the promoter is a phosphoglycerate kinase promoter (PGK) or a CMV promoter.

A helper plasmid may comprise, for example, at least one viral helper DNA sequence derived from a replication-incompetent viral genome encoding in trans all virion proteins required to package a replication incompetent AAV, and for producing virion proteins capable of packaging the replication-incompetent AAV at high titer, without the production of replication-competent AAV.

Helper plasmids for packaging AAV are known in the art, see, e.g., U.S. Patent Pub. No. 2004/0235174 A1, incorporated herein by reference. As stated therein, an AAV helper plasmid may contain as helper virus DNA sequences, by way of non-limiting example, the Ad5 genes E2A, E4 and VA, controlled by their respective original promoters or by heterologous promoters. AAV helper plasmids may additionally contain an expression cassette for the expression of a marker protein such as a fluorescent protein to permit the simple detection of transfection of a desired target cell.

The disclosure provides methods of producing rAAV viral vectors comprising transfecting a packaging cell line with any one of the AAV helper plasmids disclosed herein; and any one of the rAAV vectors disclosed herein. In some aspects, the AAV helper plasmid and rAAV vector are co-transfected into the packaging cell line. In some aspects, the cell line is a mammalian cell line, for example, human embryonic kidney (HEK) 293 cell line. The disclosure provides cells comprising any one of the rAAV vectors and/or rAAV viral vectors disclosed herein.

As used herein, the term "helper" in reference to a virus or plasmid refers to a virus or plasmid used to provide the additional components necessary for replication and packaging of any one of the rAAV vectors disclosed herein. The components encoded by a helper virus may include any genes required for virion assembly, encapsidation, genome replication, and/or packaging. For example, the helper virus or plasmid may encode necessary enzymes for the replication of the viral genome. Non-limiting examples of helper viruses and plasmids suitable for use with AAV constructs include pHELP (plasmid), adenovirus (virus), or herpesvirus (virus). In some aspects, the pHELP plasmid may be the pHELPK plasmid, wherein the ampicillin expression cassette is exchanged with a kanamycin expression cassette.

As used herein, a packaging cell (or a helper cell) is a cell used to produce viral vectors. Producing recombinant AAV viral vectors requires Rep and Cap proteins provided in trans as well as gene sequences from Adenovirus that help AAV replicate. In some aspects, Packaging/helper cells contain a plasmid is stably incorporated into the genome of the cell. In other aspects, the packaging cell may be transiently transfected. Typically, a packaging cell is a eukaryotic cell, such as a mammalian cell or an insect cell.

Kits

The isolated polynucleotides, rAAV vectors, rAAV viral vectors, compositions, and/or pharmaceutical compositions described herein may be assembled into pharmaceutical or diagnostic or research kits to facilitate their use in therapeutic, diagnostic, or research applications. In some aspects, the kits of the present disclosure include any one of the isolated polynucleotides, rAAV vectors, rAAV viral vectors, compositions, pharmaceutical compositions, host cells, isolated tissues, as described herein.

In some aspects, a kit further comprises instructions for use. Specifically, such kits may include one or more agents described herein, along with instructions describing the intended application and the proper use of these agents. In some aspects, the kit may include instructions for mixing one or more components of the kit and/or isolating and mixing a sample and applying to a subject. In some aspects, agents in a kit are in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. In some aspects, the compositions may be provided in a preservation solution (e.g., cryopreservation solution). Non-limiting examples of preservation solutions include DMSO, paraformaldehyde, and CryoStor® (Stem Cell Technologies, Vancouver, Canada). In some aspects, the preservation solution contains an amount of metalloprotease inhibitors.

In some aspects, the kit contains any one or more of the components described herein in one or more containers. Thus, in some aspects, the kit may include a container housing agents described herein. The agents may be in the form of a liquid, gel or solid (powder). The agents may be prepared sterilely, packaged in a syringe and shipped refrigerated. Alternatively, they may be housed in a vial or other container for storage. A second container may have other agents prepared sterilely. Alternatively, the kit may include the active agents premixed and shipped in a syringe, vial, tube, or other container. The kit may have one or more or all of the components required to administer the agents to a subject, such as a syringe, topical application devices, or IV needle tubing and bag.

Further Definitions

Unless the context indicates otherwise, it is specifically intended that the various features of the invention described herein can be used in any combination. Moreover, the disclosure also contemplates that, in some aspects, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless explicitly indicated otherwise, all specified aspects, embodiments, features, and terms intend to include both the recited aspect, embodiment, feature, or term and biological equivalents thereof.

The practice of the present technology will employ, unless otherwise indicated, conventional techniques of organic chemistry, pharmacology, immunology, molecular biology, microbiology, cell biology and recombinant DNA, which are within the skill of the art. See, e.g., Sambrook, Fritsch and Maniatis, Molecular Cloning: A Laboratory Manual, 2nd edition (1989); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, a Laboratory Manual, and Animal Cell Culture (RI. Freshney, ed. (1987)).

As used herein, the term "comprising" is intended to mean that the compositions and methods include the recited elements, but do not exclude others. As used herein, the transitional phrase "consisting essentially of" (and grammatical variants) is to be interpreted as encompassing the recited materials or steps and those that do not materially affect the basic and novel characteristic(s) of the recited embodiment. Thus, the term "consisting essentially of" as used herein should not be interpreted as equivalent to "comprising." "Consisting of" shall mean excluding more than trace elements of other ingredients and substantial method steps for administering the compositions disclosed herein. Aspects defined by each of these transition terms are within the scope of the present disclosure. In each instance herein any of the terms "comprising," "consisting essentially of," and "consisting of" can be replaced with either of the other two terms, while retaining their ordinary meanings. Any single term, single element, single phrase, group of terms, group of phrases, or group of elements described herein can each be specifically excluded from the claims.

All numerical designations, e.g., pH, temperature, time, concentration, and molecular weight, including ranges, are approximations which are varied (+) or (−) by increments of 1.0 or 0.1, as appropriate, or, alternatively, by a variation of +/−15%, 10%, 5%, 2%. It is to be understood, although not always explicitly stated, that all numerical designations are preceded by the term "about". It also is to be understood, although not always explicitly stated, that the reagents described herein are merely exemplary and that equivalents of such are known in the art. The term "about," as used herein when referring to a measurable value such as an amount or concentration and the like, is meant to encompass variations of 20%, 10%, 5%, 1%, 0.5%, or even 0.1% of the specified amount.

The terms "acceptable," "effective," or "sufficient" when used to describe the selection of any components, ranges, dose forms, etc. disclosed herein intend that said component, range, dose form, etc. is suitable for the disclosed purpose.

Also, as used herein, "and/or" refers to and encompasses any and all possible combinations of one or more of the associated listed items, as well as the lack of combinations when interpreted in the alternative ("or").

Unless specifically recited, the term "host cell" includes a eukaryotic host cell, including, for example, fungal cells, yeast cells, higher plant cells, insect cells and mammalian cells. Non-limiting examples of eukaryotic host cells include simian, bovine, porcine, murine, rat, avian, reptilian and human, e.g., HEK293 cells and 293T cells.

The term "isolated" as used herein refers to molecules or biologicals or cellular materials being substantially free from other materials.

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising, consisting essentially of, or consisting of purine and pyrimidine bases or other natural, chemically or biochemically modified, non-natural, or derivatized nucleotide bases.

A "gene" refers to a polynucleotide containing at least one open reading frame (ORF) that is capable of encoding a particular polypeptide or protein. A "gene product" or, alternatively, a "gene expression product" refers to the amino acid sequence (e.g., peptide or polypeptide) generated when a gene is transcribed and translated.

As used herein, "expression" refers to the two-step process by which polynucleotides are transcribed into mRNA and/or the process by which the transcribed mRNA is subsequently translated into peptides, polypeptides, or proteins. If the polynucleotide is derived from genomic DNA, expression may include splicing of the mRNA in a eukaryotic cell.

"Under transcriptional control" is a term well understood in the art and indicates that transcription of a polynucleotide sequence, usually a DNA sequence, depends on its being operatively linked to an element that contributes to the initiation of, or promotes, transcription. "Operatively linked" intends that the polynucleotides are arranged in a manner that allows them to function in a cell. In one aspect, promoters can be operatively linked to the downstream sequences.

The term "encode" as it is applied to polynucleotides and/or nucleic acid sequences refers to a polynucleotide and/or nucleic acid sequence which is said to "encode" a polypeptide if its base sequence is identical to the base sequence of the RNA transcript (e.g. mRNA transcript) that is translated into the polypeptide and/or a fragment thereof. The antisense strand is the complement of such a nucleic acid, and the encoding sequence can be deduced therefrom.

The term "protein", "peptide" and "polypeptide" are used interchangeably and in their broadest sense to refer to a compound of two or more subunits of amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise, consist essentially of, or consist of a protein's or peptide's sequence. As used herein the term "amino acid" refers to either natural and/or unnatural or synthetic amino acids, including glycine and both the D and L optical isomers, amino acid analogs and peptidomimetics.

As used herein, the term "signal peptide" or "signal polypeptide" intends an amino acid sequence usually present at the N-terminal end of newly synthesized secretory or membrane polypeptides or proteins. It acts to direct the polypeptide to a specific cellular location, e.g. across a cell membrane, into a cell membrane, or into the nucleus. In some aspects, the signal peptide is removed following localization. Examples of signal peptides are well known in the art. Non-limiting examples are those described in U.S. Pat. Nos. 8,853,381, 5,958,736, and 8,795,965. In some aspects, the signal peptide can be an IDUA signal peptide.

The terms "equivalent" or "biological equivalent" are used interchangeably when referring to a particular molecule, biological material, or cellular material and intend those having minimal homology while still maintaining desired structure or functionality. Non-limiting examples of equivalent polypeptides include a polypeptide having at least about 60%, at least about 65%, at least about 70%, at least about 75%, at least about 80%, at least about 85%, at least about 90%, at least about 95% identity or at least about 99% identity to a reference polypeptide (for instance, a wild-type polypeptide); or a polypeptide which is encoded by a polynucleotide having at least about 70%, at least about 75%, at least about 80%, at least about 85%, at least about 90%, at least about 95% identity, at least about 97% sequence identity or at least about 99% sequence identity to the reference polynucleotide (for instance, a wild-type polynucleotide).

"Homology" or "identity" or "similarity" refers to sequence similarity between two peptides or between two nucleic acid molecules. Percent identity can be determined by comparing a position in each sequence that may be aligned for purposes of comparison. When a position in the compared sequence is occupied by the same base or amino acid, then the molecules are identical at that position. A degree of identity between sequences is a function of the number of matching positions shared by the sequences. "Unrelated" or "non-homologous" sequences share less than 40% identity, less than 25% identity, with one of the sequences of the present disclosure. Alignment and percent sequence identity may be determined for the nucleic acid or amino acid sequences provided herein by importing said nucleic acid or amino acid sequences into and using ClustalW (available at https://genome.jp/tools-bin/clustalw/). For example, the ClustalW parameters used for performing the protein sequence alignments found herein were generated using the Gonnet (for protein) weight matrix. In some aspects, the ClustalW parameters used for performing nucleic acid sequence alignments using the nucleic acid sequences found herein are generated using the ClustalW (for DNA) weight matrix.

As used herein, amino acid modifications may be amino acid substitutions, amino acid deletions or amino acid insertions. Amino acid substitutions may be conservative amino acid substitutions or non-conservative amino acid substitutions. A conservative replacement (also called a conservative mutation, a conservative substitution or a conservative variation) is an amino acid replacement in a protein that changes a given amino acid to a different amino acid with similar biochemical properties (e.g., charge, hydrophobicity or size). As used herein, "conservative variations" refer to the replacement of an amino acid residue by another, biologically similar residue. Examples of conservative variations include the substitution of one hydrophobic residue such as isoleucine, valine, leucine or methionine for another; or the substitution of one charged or polar residue for another, such as the substitution of arginine for lysine, glutamic acid for aspartic acid, glutamine for asparagine, and the like. Other illustrative examples of conservative substitutions include the changes of: alanine to serine; asparagine to glutamine or histidine; aspartate to glutamate; cysteine to serine; glycine to proline; histidine to asparagine or glutamine; lysine to arginine, glutamine, or glutamate; phenylalanine to tyrosine, serine to threonine; threonine to serine; tryptophan to tyrosine; tyrosine to tryptophan or phenylalanine; and the like.

A polynucleotide disclosed herein can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "plasmid" is a DNA molecule that is typically separate from and capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or, alternatively, the proteins produced may act as toxins under similar circumstances. It is known in the art that while plasmid vectors often exist as extrachromosomal circular DNA molecules, plasmid vectors may also be designed to be stably integrated into a host chromosome either randomly or in a targeted manner, and such integration may be accomplished using either a circular plasmid or a plasmid that has been linearized prior to introduction into the host cell.

"Plasmids" used in genetic engineering are called "plasmid vectors". Many plasmids are commercially available for such uses. The gene to be replicated is inserted into copies of a plasmid containing genes that make cells resistant to particular antibiotics, and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria or eukaryotic cells containing a plasmid harboring the gene of interest, which can be induced to produce large amounts of proteins from the inserted gene.

In aspects where gene transfer is mediated by a DNA viral vector, such as an adenovirus (Ad) or adeno-associated virus (AAV), a vector construct refers to the polynucleotide comprising, consisting essentially of, or consisting of the viral genome or part thereof, and a transgene.

The term "tissue" is used herein to refer to tissue of a living or deceased organism or any tissue derived from or designed to mimic a living or deceased organism. The tissue may be healthy, diseased, and/or have genetic mutations. The biological tissue may include any single tissue (e.g., a collection of cells that may be interconnected), or a group of tissues making up an organ or part or region of the body of an organism. The tissue may comprise, consist essentially of, or consist of a homogeneous cellular material or it may be a composite structure such as that found in regions of the body including the thorax which for instance can include lung tissue, skeletal tissue, and/or muscle tissue. Exemplary tissues include, but are not limited to those derived from liver, lung, thyroid, skin, pancreas, blood vessels, bladder, kidneys, brain, biliary tree, duodenum, abdominal aorta, iliac vein, heart and intestines, including any combination thereof.

EXAMPLES

Example 1—Administration of a Gene Therapy Via a Vagus Nerve Results in Exogenous Protein Expression in the Autonomic Nervous System The following non-limiting example demonstrates that the administration of an rAAV viral vector via a vagus nerve results in exogenous protein expression in the autonomic nervous system.

AAV9 viral vectors comprising a nucleic acid sequence encoding for a GFP reporter protein were injected into the left vagus nerve of a rat. GFP expression was then assessed via fluorescence microscopy. As shown in FIG. 1, GFP expression was observed in the vagal circuits linking the central nervous system and the peripheral nervous system, including in the vagus nerve (denoted by an arrow in FIG. 1, the dorsal motor nucleus of the vagus (denoted by an asterix in FIG. 1) and the nucleus *ambiguus* (denoted by a star in FIG. 1). These results indicate that the administration of a gene therapy, such as an rAAV viral vector, via a vagus nerve can be used to effectively target the gene therapy to the autonomic nervous system of a subject, thereby allowing for the expression of an exogenous protein and/or nucleic acid.

Example 2—Administration of a Gene Therapy Via a Vagus Nerve Results in Exogenous Protein Expression Even in Subjects that are Pre-Immunized to the Gene Therapy The following non-limiting example demonstrates that the administration of an rAAV viral vector via a vagus nerve results in exogenous protein expression even in a subject that has been pre-immunized to the rAAV viral vector (i.e. has neutralizing antibodies against the rAAV viral vector and/or is seropositive for an AAV particle with the same serotype).

Figure 2:
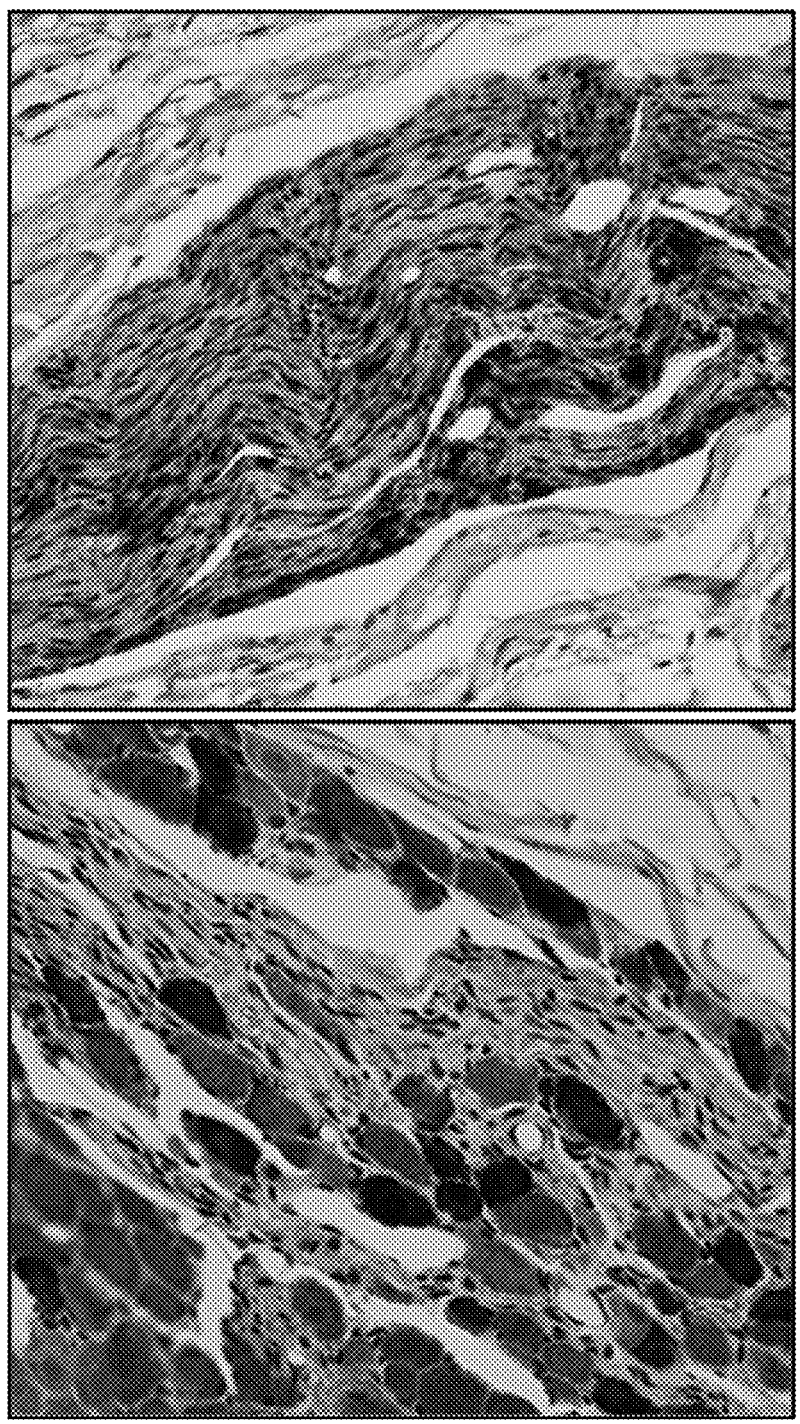
FIG. 2 is a series of images showing GFP expression following administration of an AAV9/GFP viral vector via the left vagus nerve in a rat pre-immunized by intrathecal injection of AAV9/GAN. Left panel: neuronal cell bodies of the left nodose ganglia. Right panel: left cervical vagus nerve fibers.

In a first experiment, rats were pre-immunized to an AAV9 viral vector by intrathecal injection of an AAV9 viral vector comprising a nucleic acid encoding a gigaxonin (GAN) polypeptide. The rats were subsequently administered an AAV9 viral vector comprising a nucleic acid encoding a GFP reporter protein via injection into the left vagus nerve. GFP expression was then analyzed. As shown in FIG. 2, strong GFP expression was observed in the peripheral nervous system, including the neuronal cell bodies of the left nodose ganglia (left panel of FIG. 2) and the left cervical vagus nerve fibers (right panel of FIG. 2).

Figure 3:
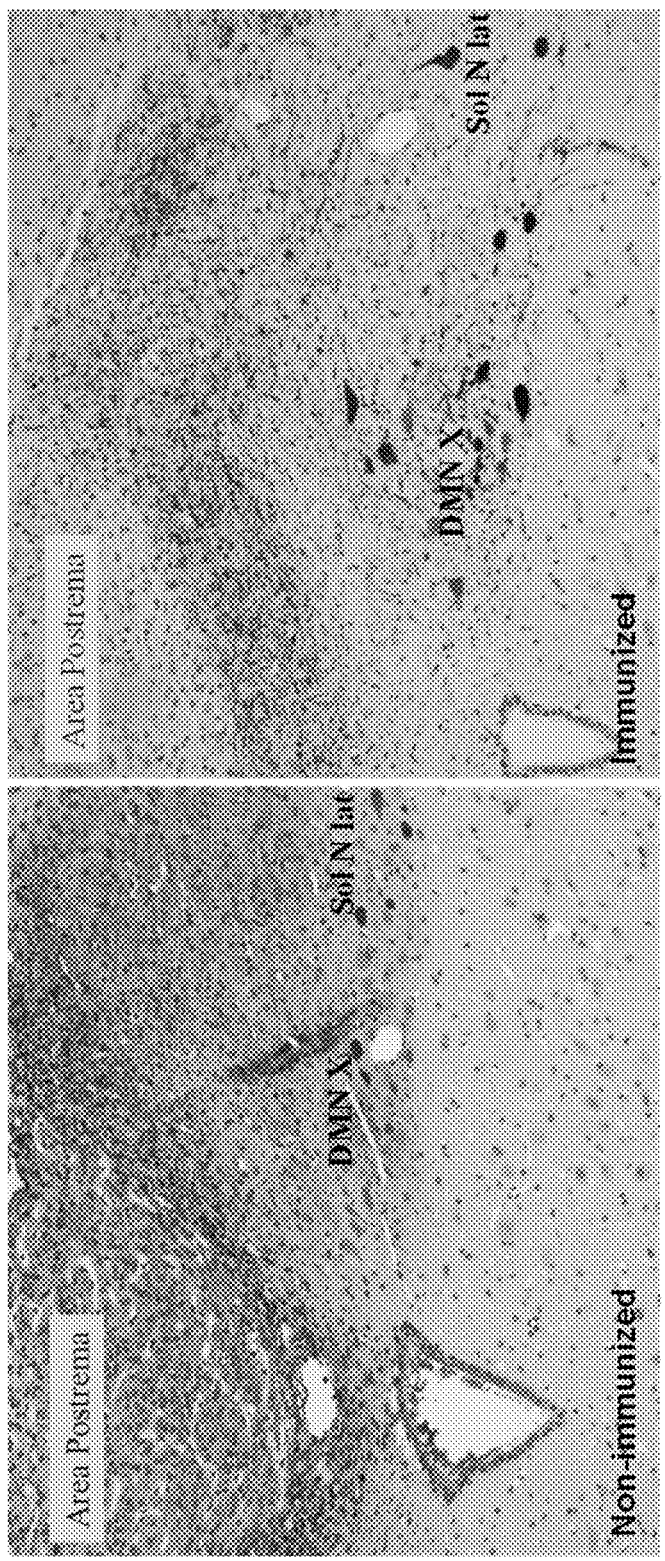
FIG. 3 is a series of images showing GFP expression in the brain of rats following a left vagus nerve injection of AAV9/GFP in non-immunized rats (left panel) or rats pre-immunized to AAV9 (right panel). The dorsal motor nucleus of the vagus is indicated by "DMN X" and the solitary nucleus is indicated by "Sol N lat".

In a second experiment, rats were either left untreated (hereafter referred to as "non-immunized rats") or were pre-immunized to an AAV9 viral vector by intrathecal expression of an AAV9 viral vector (hereafter referred to as "immunized rats"). The rats were subsequently administered an AAV9 viral vector comprising a nucleic acid encoding a GFP reporter protein via injection into the left vagus nerve. GFP expression was then analyzed. As shown in FIG. 3, strong GFP expression was observed even in the pre-immunized rats (right panel), including expression in the dorsal motor nucleus of the vagus (denoted "DMN X" in FIG. 3) and the solitary nucleus (denoted "Sol N lat" in FIG. 3).

These results demonstrate that in subjects that may have neutralizing antibodies against a particular serotype of AAV particle (e.g. due to the previous administration of an AAV-based gene therapy), administration of a subsequent AAV-based gene therapy via the vagus nerve can avoid treatment neutralization and effectively drive exogenous protein expression.

Example 3—Administration of a Gene Therapy Via a Vagus Nerve Effectively Treats Autonomic Dysfunction in a Rat Model of Giant Axonal Neuropathy The following is a non-limiting example that demonstrates that the administration of an rAAV viral vector via injection into a vagus nerve can effectively treat Giant Axonal Neuropathy, and more specifically, the autonomic dysfunctions associated with Giant Axonal Neuropathy.

In the following experiment, a rat model of Giant Axonal Neuropathy was tested. The rat model of Giant Axonal Neuropathy was established by introducing a gene encoding for a mutant GAN polypeptide into the rats. These rats are herein referred to as GAN Knock-in (KI) rats.

At four months of age, the GAN KI rats were either: a) treated with a vehicle control (hereafter "GAN KI"); b) treated with an AAV9 viral vector comprising a nucleic acid encoding for a GAN polypeptide (AAV9/GAN) via intrathecal injection (hereafter "GAN KI IT"); or c) treated with AAV9/GAN administered both via an intrathecal injection and via injection into the left vagus nerve (hereafter "GAN KI IT+VN"). At 20 months of age, the rats then received an intraperitoneal injection of 1 mg/kg pilocarpine and physiological responses associated with autonomic function were recorded using wireless telemetry devices implanted in the rats. The results of this analysis are shown in FIG. 4.

Figure 4:
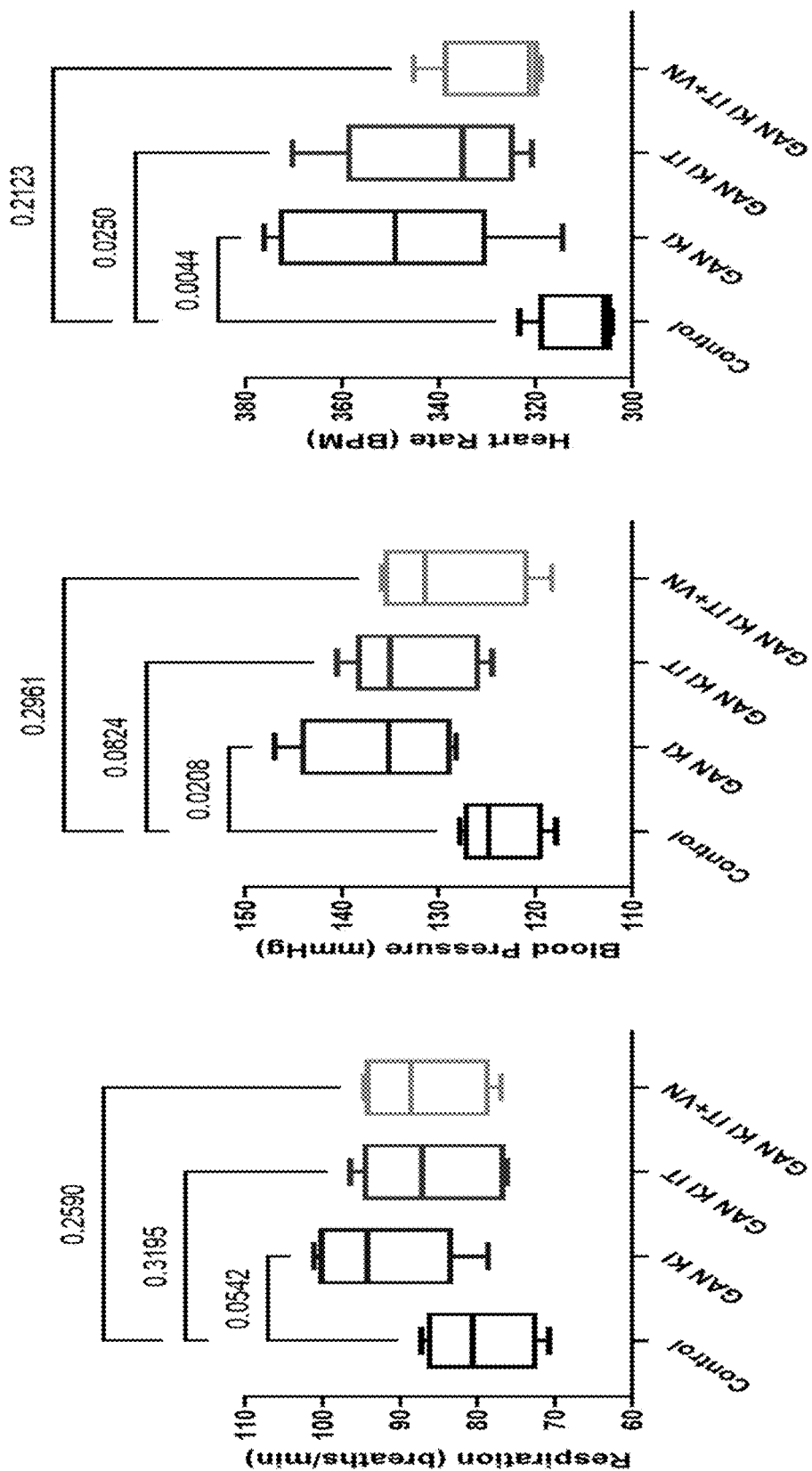
FIG. 4 is a series of graphs showing physiological responses associated with autonomic function in wild-type and mutant GAN knock-in mice challenged with pilocarpine and treated using the compositions and methods of the present disclosure. Graphical data are represented as box and whisker plots where error bars represent maximum and minimum values and the boxed line represents the median.

As shown in FIG. 4, when challenged with pilocarpine treatment GAN KI rats showed an abnormal regulation of the autonomic response as compared to control rats for respiration (left panel of FIG. 4), blood pressure (middle panel of FIG. 4), and heart rate (right panel of FIG. 4). In contrast, IT only delivery (GAN KI IT) of AAV9/GAN improved respiration and blood pressure. Combined IT+VN delivery (GAN KI IT+VN) of AAV9/GAN showed greater efficacy than IT alone with normalization of respiration, blood pressure and heart rate responses as compared to control, wild-type rats. 4 control rats were analyzed and 5 GAN KI rats per treatment group were analyzed.

These results demonstrate that the administration of an rAAV viral vector comprising a nucleic acid encoding for a GAN polypeptide via injection into a vagus nerve can effectively treat Giant Axonal Neuropathy, and more specifically, the autonomic dysfunctions associated with Giant Axonal Neuropathy, including when the administration via the vagus nerve is used in combination with an intrathecal administration of the rAAV viral vector.

What is claimed is:

1. A method of treating a disease and/or disorder in a subject comprising administering to the subject at least one therapeutically effective amount of a recombinant adeno-associated virus (rAAV) viral vector by injecting the at least one therapeutically effective amount of the rAAV viral vector into a vagus nerve of the subject, wherein the rAAV viral vector comprises:
(i) an AAV capsid protein; and
(ii) an rAAV vector, wherein the rAAV vector comprises in a 5' to 3' direction:
   a) a first AAV ITR sequence;
   b) a promoter sequence;
   c) a transgene nucleic acid molecule, wherein the transgene nucleic acid molecule comprises a nucleic acid sequence encoding for a gigaxonin (GAN) polypeptide;
   d) a polyA sequence; and
   e) a second AAV ITR sequence;
wherein the nucleic acid sequence encoding the GAN polypeptide comprises a nucleic acid sequence set forth in SEQ ID NO: 3.

2. The method of claim 1, wherein the vagus nerve is a left vagus nerve of the subject.

3. The method of claim 1, wherein the disease and/or disorder is a neurological disease and/or disorder.

4. The method of claim 3, wherein the neurological disease and/or disorder is characterized by at least one autonomic dysfunction, and wherein administration of the at least one therapeutically effective amount of the rAAV viral vector via injection into the vagus nerve alleviates at least one symptom of the at least one autonomic dysfunction.

5. The method of claim 4, wherein the at least one symptom is selected from dysarthria, dysphagia, inadequate control of gastrointestinal tract motility, inadequate control of blood pressure, respiratory difficulties, orthostatic hypotension, sweating abnormalities, inadequate control of urinary tract, sexual dysfunction, and any combination thereof.

6. The method of claim 1, wherein the disease and/or disorder is selected from Spinal muscular atrophy, Friedrich's ataxia, CLN3 Batten, CLN6 Batten, CLN7 Batten, Epileptic encephalopathy, Leigh Syndrome, Charcot Marie Tooth disease, Giant Axonal Neuropathy, Lafora disease, SLC13A5 Epileptic Encephalopathy, Congenital Disorder of Glycosylation, Type Iq, Kahrizi Syndrome, Angelman Syndrome, Rett Syndrome, Spastic paraplegia, Alternating hemiplegia of childhood, and Zellweger spectrum disorder.

7. The method of claim 6, wherein the disease and/or disorder is Giant Axonal Neuropathy.

8. The method of claim 1, wherein the GAN polypeptide comprises an amino acid sequence set forth in SEQ ID NO: 1.

9. The method of claim 1, wherein the promoter sequence comprises a nucleic acid sequence set forth in SEQ ID NO: 8.

10. The method of claim 1, wherein the polyA sequence comprises a nucleic acid sequence set forth in SEQ ID NO: 9.

11. The method of claim 1, wherein the promoter sequence comprises a nucleic acid sequence set forth in SEQ ID NO: 8; the GAN polypeptide comprises a nucleic acid sequence set forth in SEQ ID NO: 3; and the polyA sequence comprises a nucleic acid sequence set forth in SEQ ID NO: 9.

12. The method of claim 11, wherein the rAAV vector comprises a nucleic acid sequence set forth in SEQ ID NO: 10.

13. The method of claim 1, wherein the AAV capsid protein is an AAV9 capsid protein.

14. The method of claim 1, wherein the rAAV viral vector is administered in an amount of about $3.5\times10^{13}$ to about $3.5\times10^{14}$ viral particles.

15. The method of claim 1, wherein the subject has neutralizing antibodies against the rAAV viral vector.

16. A method of treating Giant Axonal Neuropathy in a subject comprising:
   a) intrathecally administering a first therapeutically effective amount of an rAAV viral vector to the subject and
   b) administering an at least second therapeutically effective amount of the rAAV viral vector by injecting the at least second therapeutically effective amount of the rAAV viral vector into a left vagus nerve of the subject, wherein the rAAV viral vector comprises:
      (i) an AAV9 capsid protein; and
      (ii) an rAAV vector, wherein the rAAV vector comprises a nucleic acid sequence set forth in SEQ ID NO: 10.

17. The method of claim 16, wherein the first therapeutically effective amount of the rAAV viral vector and the at least second therapeutically effective amount of the rAAV viral vector are administered sequentially.

18. The method of claim 16, wherein the first therapeutically effective amount of the rAAV viral vector and the at least second therapeutically effective amount of the rAAV viral vector are administered concurrently.

* * * * *

SEQUENCE LISTING

```
<160> NUMBER OF SEQ ID NOS: 11

<210> SEQ ID NO 1
<211> LENGTH: 597
<212> TYPE: PRT
<213> ORGANISM: Homo sapiens

<400> SEQUENCE: 1

Met Ala Glu Gly Ser Ala Val Ser Asp Pro Gln His Ala Ala Arg Leu
1               5                   10                  15

Leu Arg Ala Leu Ser Ser Phe Arg Glu Glu Ser Arg Phe Cys Asp Ala
            20                  25                  30

His Leu Val Leu Asp Gly Glu Glu Ile Pro Val Gln Lys Asn Ile Leu
        35                  40                  45

Ala Ala Ala Ser Pro Tyr Ile Arg Thr Lys Leu Asn Tyr Asn Pro Pro
    50                  55                  60

Lys Asp Asp Gly Ser Thr Tyr Lys Ile Glu Leu Glu Gly Ile Ser Val
65                  70                  75                  80

Met Val Met Arg Glu Ile Leu Asp Tyr Ile Phe Ser Gly Gln Ile Arg
                85                  90                  95

Leu Asn Glu Asp Thr Ile Gln Asp Val Val Gln Ala Ala Asp Leu Leu
            100                 105                 110

Leu Leu Thr Asp Leu Lys Thr Leu Cys Cys Glu Phe Leu Glu Gly Cys
        115                 120                 125
```

```
Ile Ala Ala Glu Asn Cys Ile Gly Ile Arg Asp Phe Ala Leu His Tyr
            130                 135                 140

Cys Leu His His Val His Tyr Leu Ala Thr Glu Tyr Leu Glu Thr His
145                 150                 155                 160

Phe Arg Asp Val Ser Ser Thr Glu Glu Phe Leu Glu Leu Ser Pro Gln
                165                 170                 175

Lys Leu Lys Glu Val Ile Ser Leu Glu Lys Leu Asn Val Gly Asn Glu
                180                 185                 190

Arg Tyr Val Phe Glu Ala Val Ile Arg Trp Ile Ala His Asp Thr Glu
                195                 200                 205

Ile Arg Lys Val His Met Lys Asp Val Met Ser Ala Leu Trp Val Ser
210                 215                 220

Gly Leu Asp Ser Ser Tyr Leu Arg Glu Gln Met Leu Asn Glu Pro Leu
225                 230                 235                 240

Val Arg Glu Ile Val Lys Glu Cys Ser Asn Ile Pro Leu Ser Gln Pro
                245                 250                 255

Gln Gln Gly Glu Ala Met Leu Ala Asn Phe Lys Pro Arg Gly Tyr Ser
                260                 265                 270

Glu Cys Ile Val Thr Val Gly Gly Glu Glu Arg Val Ser Arg Lys Pro
                275                 280                 285

Thr Ala Ala Met Arg Cys Met Cys Pro Leu Tyr Asp Pro Asn Arg Gln
                290                 295                 300

Leu Trp Ile Glu Leu Ala Pro Leu Ser Met Pro Arg Ile Asn His Gly
305                 310                 315                 320

Val Leu Ser Ala Glu Gly Phe Leu Phe Val Phe Gly Gly Gln Asp Glu
                325                 330                 335

Asn Lys Gln Thr Leu Ser Ser Gly Glu Lys Tyr Asp Pro Asp Ala Asn
                340                 345                 350

Thr Trp Thr Ala Leu Pro Pro Met Asn Glu Ala Arg His Asn Phe Gly
                355                 360                 365

Ile Val Glu Ile Asp Gly Met Leu Tyr Ile Leu Gly Gly Glu Asp Gly
                370                 375                 380

Glu Lys Glu Leu Ile Ser Met Glu Cys Tyr Asp Ile Tyr Ser Lys Thr
385                 390                 395                 400

Trp Thr Lys Gln Pro Asp Leu Thr Met Val Arg Lys Ile Gly Cys Tyr
                405                 410                 415

Ala Ala Met Lys Lys Ile Tyr Ala Met Gly Gly Ser Tyr Gly
                420                 425                 430

Lys Leu Phe Glu Ser Val Glu Cys Tyr Asp Pro Arg Thr Gln Gln Trp
                435                 440                 445

Thr Ala Ile Cys Pro Leu Lys Glu Arg Arg Phe Gly Ala Val Ala Cys
                450                 455                 460

Gly Val Ala Met Glu Leu Tyr Val Phe Gly Gly Val Arg Ser Arg Glu
465                 470                 475                 480

Asp Ala Gln Gly Ser Glu Met Val Thr Cys Lys Ser Glu Phe Tyr His
                485                 490                 495

Asp Glu Phe Lys Arg Trp Ile Tyr Leu Asn Asp Gln Asn Leu Cys Ile
                500                 505                 510

Pro Ala Ser Ser Ser Phe Val Tyr Gly Ala Val Pro Ile Gly Ala Ser
                515                 520                 525

Ile Tyr Val Ile Gly Asp Leu Asp Thr Gly Thr Asn Tyr Asp Tyr Val
                530                 535                 540

Arg Glu Phe Lys Arg Ser Thr Gly Thr Trp His His Thr Lys Pro Leu
```

Leu Pro Ser Asp Leu Arg Arg Thr Gly Cys Ala Ala Leu Arg Ile Ala
545                 550                 555                 560

Asn Cys Lys Leu Phe Arg Leu Gln Leu Gln Gln Gly Leu Phe Arg Ile
        565                 570                 575

Arg Val His Ser Pro
        580                 585                 590

Arg Val His Ser Pro
        595

<210> SEQ ID NO 2
<211> LENGTH: 596
<212> TYPE: PRT
<213> ORGANISM: Homo sapiens

<400> SEQUENCE: 2

Ala Glu Gly Ser Ala Val Ser Asp Pro Gln His Ala Ala Arg Leu Leu
1               5                   10                  15

Arg Ala Leu Ser Ser Phe Arg Glu Glu Ser Arg Phe Cys Asp Ala His
            20                  25                  30

Leu Val Leu Asp Gly Glu Glu Ile Pro Val Gln Lys Asn Ile Leu Ala
        35                  40                  45

Ala Ala Ser Pro Tyr Ile Arg Thr Lys Leu Asn Tyr Asn Pro Pro Lys
50                  55                  60

Asp Asp Gly Ser Thr Tyr Lys Ile Glu Leu Glu Gly Ile Ser Val Met
65                  70                  75                  80

Val Met Arg Glu Ile Leu Asp Tyr Ile Phe Ser Gly Gln Ile Arg Leu
                85                  90                  95

Asn Glu Asp Thr Ile Gln Asp Val Val Gln Ala Ala Asp Leu Leu Leu
            100                 105                 110

Leu Thr Asp Leu Lys Thr Leu Cys Cys Glu Phe Leu Glu Gly Cys Ile
        115                 120                 125

Ala Ala Glu Asn Cys Ile Gly Ile Arg Asp Phe Ala Leu His Tyr Cys
130                 135                 140

Leu His His Val His Tyr Leu Ala Thr Glu Tyr Leu Glu Thr His Phe
145                 150                 155                 160

Arg Asp Val Ser Ser Thr Glu Glu Phe Leu Glu Leu Ser Pro Gln Lys
                165                 170                 175

Leu Lys Glu Val Ile Ser Leu Glu Lys Leu Asn Val Gly Asn Glu Arg
            180                 185                 190

Tyr Val Phe Glu Ala Val Ile Arg Trp Ile Ala His Asp Thr Glu Ile
        195                 200                 205

Arg Lys Val His Met Lys Asp Val Met Ser Ala Leu Trp Val Ser Gly
210                 215                 220

Leu Asp Ser Ser Tyr Leu Arg Glu Gln Met Leu Asn Glu Pro Leu Val
225                 230                 235                 240

Arg Glu Ile Val Lys Glu Cys Ser Asn Ile Pro Leu Ser Gln Pro Gln
                245                 250                 255

Gln Gly Glu Ala Met Leu Ala Asn Phe Lys Pro Arg Gly Tyr Ser Glu
            260                 265                 270

Cys Ile Val Thr Val Gly Gly Glu Glu Arg Val Ser Arg Lys Pro Thr
        275                 280                 285

Ala Ala Met Arg Cys Met Cys Pro Leu Tyr Asp Pro Asn Arg Gln Leu
290                 295                 300

Trp Ile Glu Leu Ala Pro Leu Ser Met Pro Arg Ile Asn His Gly Val
305                 310                 315                 320

```
Leu Ser Ala Glu Gly Phe Leu Phe Val Phe Gly Gly Gln Asp Glu Asn
                325                 330                 335

Lys Gln Thr Leu Ser Ser Gly Glu Lys Tyr Asp Pro Asp Ala Asn Thr
            340                 345                 350

Trp Thr Ala Leu Pro Pro Met Asn Glu Ala Arg His Asn Phe Gly Ile
        355                 360                 365

Val Glu Ile Asp Gly Met Leu Tyr Ile Leu Gly Gly Glu Asp Gly Glu
    370                 375                 380

Lys Glu Leu Ile Ser Met Glu Cys Tyr Asp Ile Tyr Ser Lys Thr Trp
385                 390                 395                 400

Thr Lys Gln Pro Asp Leu Thr Met Val Arg Lys Ile Gly Cys Tyr Ala
                405                 410                 415

Ala Met Lys Lys Lys Ile Tyr Ala Met Gly Gly Gly Ser Tyr Gly Lys
            420                 425                 430

Leu Phe Glu Ser Val Glu Cys Tyr Asp Pro Arg Thr Gln Gln Trp Thr
        435                 440                 445

Ala Ile Cys Pro Leu Lys Glu Arg Arg Phe Gly Ala Val Ala Cys Gly
    450                 455                 460

Val Ala Met Glu Leu Tyr Val Phe Gly Gly Val Arg Ser Arg Glu Asp
465                 470                 475                 480

Ala Gln Gly Ser Glu Met Val Thr Cys Lys Ser Glu Phe Tyr His Asp
                485                 490                 495

Glu Phe Lys Arg Trp Ile Tyr Leu Asn Asp Gln Asn Leu Cys Ile Pro
            500                 505                 510

Ala Ser Ser Ser Phe Val Tyr Gly Ala Val Pro Ile Gly Ala Ser Ile
        515                 520                 525

Tyr Val Ile Gly Asp Leu Asp Thr Gly Thr Asn Tyr Asp Tyr Val Arg
    530                 535                 540

Glu Phe Lys Arg Ser Thr Gly Thr Trp His His Thr Lys Pro Leu Leu
545                 550                 555                 560

Pro Ser Asp Leu Arg Arg Thr Gly Cys Ala Ala Leu Arg Ile Ala Asn
                565                 570                 575

Cys Lys Leu Phe Arg Leu Gln Leu Gln Gln Gly Leu Phe Arg Ile Arg
            580                 585                 590

Val His Ser Pro
        595

<210> SEQ ID NO 3
<211> LENGTH: 1794
<212> TYPE: DNA
<213> ORGANISM: Artificial Sequence
<220> FEATURE:
<223> OTHER INFORMATION: Synthetic Sequence

<400> SEQUENCE: 3
atggctgaag gcagtgcagt ttccgatcct caacatgcgg ccagacttct ccgagcgctc      60
tctagcttta gggaagagag cagattttgc gatgcacacc tggtcctcga cggggaagag     120
attcccgtgc aaaagaacat tctggccgct gccagcccat acattaggac caagctgaac     180
tataacccac cgaaagacga cgggtctaca tacaagatag agctggaagg gatctcagta     240
atggtgatgc gggagatact ggactatatc ttctctggtc agattcgcct caatgaggat     300
acgattcaag atgtagtcca ggccgctgat cttctgctgc tcactgatct caagaccctg     360
tgttgtgagt cctcgagggg ctgcatcgcc gcagaaaact gcatcggtat tcgggatttc     420
gcgctgcact attgccttca ccacgtgcat tatctcgcca ccgaatatct tgagactcat     480
```

```
tttcgggatg taagctcaac agaagaattt cttgaactga gtcctcaaaa gttgaaggaa      540
gtcatctcat tggaaaagct caatgtcggc aatgagcgat acgtgttcga agcagtgatc      600
cggtggattg cccatgacac ggagattcgc aaagtgcaca tgaaagatgt gatgtctgca      660
ctttgggtta gtggcctgga cagctcctac ttgcgggagc agatgttgaa tgagcccctc      720
gtgcgggaaa tcgtgaaaga gtgtagtaac atcccgctct ctcaacctca gcagggagag      780
gcaatgctgg ctaactttaa gcctcggggc tactcagagt gcattgtcac gtgggaggc       840 gaagagaggg tgagcagaaa gcccactgcc gccatgcgct gtatgtgccc cctgtacgac      900
cctaaccgcc agctgtggat agaactggcc cctctgtcta tgccaaggat aaaccatggt      960
gttctgagtg ccgagggctt tctcttcgtt ttcggcggac aggacgagaa caagcagacg     1020
ctcagctccg gcgagaagta cgacccagat gctaacacat ggacggcgct gcccccctatg    1080 aatgaggctc gccataactt cgggattgta gagattgacg gaatgctgta cattctcgga     1140
ggagaggatg gagagaaaga acttatctca atggaatgtt acgacatcta ctccaagact     1200
tggactaaac agccagacct gacaatggtt aggaagatcg gatgctacgc agccatgaaa     1260
aagaaaatct atgccatggg cggaggatca tacggtaaac tgtttgagtc tgtcgaatgc     1320
tatgatccca gaacccagca gtggaccgcc atatgtccac tgaaagaacg gcgattcggg     1380
gctgtcgcat gcggtgtagc tatggagctg tatgttttg gcggcgtgag aagtagggag      1440
gacgctcaag ggtcagaaat ggtgacatgc aaaagcgagt ctatcacga cgagtttaag      1500 cgatggatct atctgaatga ccagaatttg tgtataccag catctagctc cttcgtgtat     1560
ggagcggtcc ctattggcgc tagcatctac gtcatcgggg atttggacac aggcaccaat     1620
tacgattatg tgagagagtt caaaaggagc actggcactt ggcatcacac caagccactc     1680
ctgccgtccg accttcgaag aacaggttgt gcagcattgc ggatcgccaa ctgcaaactg     1740
ttccgcctgc agcttcaaca ggggctcttt agaataaggg tgcacagtcc ctga           1794
```

<210> SEQ ID NO 4
<211> LENGTH: 1791
<212> TYPE: DNA
<213> ORGANISM: Artificial Sequence
<220> FEATURE:
<223> OTHER INFORMATION: Synthetic Sequence

<400> SEQUENCE: 4

```
gctgaaggca gtgcagtttc cgatcctcaa catgcggcca gacttctccg agcgctctct       60
agctttaggg aagagagcag attttgcgat gcacacctgg tcctcgacgg ggaagagatt      120
cccgtgcaaa agaacattct ggccgctgcc agcccataca ttaggaccaa gctgaactat      180
aacccaccga agacgacgg gtctacatac aagatagagc tggaagggat ctcagtaatg       240
gtgatgcggg agatactgga ctatatcttc tctggtcaga ttcgcctcaa tgaggatacg      300
attcaagatg tagtccaggc cgctgatctt ctgctgctca ctgatctcaa gaccctgtgt      360
tgtgagttcc tcgagggctg catcgccgca gaaaactgca tcggtattcg ggatttcgcg      420
ctgcactatt gccttcacca cgtgcattat ctcgccaccg aatatcttga gactcatttt      480
cgggatgtaa gctcaacaga agaatttctt gaactgagtc ctcaaaagtt gaaggaagtc     540
atctcattgg aaaagctcaa tgtcggcaat gagcgatacg tgttcgaagc agtgatccgg     600
tggattgccc atgacacgga gattcgcaaa gtgcacatga agatgtgat gtctgcactt     660 tgggttagtg gcctggacag ctcctacttg cgggagcaga tgttgaatga gcccctcgtg    720
```

| | |
|---|---|
| cgggaaatcg tgaaagagtg tagtaacatc ccgctctctc aacctcagca gggagaggca | 780 |
| atgctggcta actttaagcc tcggggctac tcagagtgca ttgtcactgt ggaggcgaa | 840 |
| gagagggtga gcagaaagcc cactgccgcc atgcgctgta tgtgcccct gtacgaccct | 900 |
| aaccgccagc tgtggataga actgcccct ctgtctatgc caaggataaa ccatggtgtt | 960 |
| ctgagtgccg agggctttct cttcgttttc ggcggacagg acgagaacaa gcagacgctc | 1020 |
| agctccggcg agaagtacga cccagatgct aacacatgga cggcgctgcc ccctatgaat | 1080 |
| gaggctcgcc ataacttcgg gattgtagag attgacggaa tgctgtacat tctcggagga | 1140 |
| gaggatggag agaaagaact tatctcaatg gaatgttacg acatctactc caagacttgg | 1200 |
| actaaacagc cagacctgac aatggttagg aagatcggat gctacgcagc catgaaaaag | 1260 |
| aaaatctatg ccatgggcgg aggatcatac ggtaaactgt ttgagtctgt cgaatgctat | 1320 |
| gatcccagaa cccagcagtg gaccgccata tgtccactga agaacggcg attcggggct | 1380 |
| gtcgcatgcg gtgtagctat ggagctgtat gttttggcg cgtgagaag tagggaggac | 1440 |
| gctcaagggt cagaaatggt gacatgcaaa agcgagttct atcacgacga gtttaagcga | 1500 |
| tggatctatc tgaatgacca gaatttgtgt ataccagcat ctagctcctt cgtgtatgga | 1560 |
| gcggtcccta ttggcgctag catctacgtc atcggggatt tggacacagg caccaattac | 1620 |
| gattatgtga gagagttcaa aaggagcact ggcacttggc atcacaccaa gccactcctg | 1680 |
| ccgtccgacc ttcgaagaac aggttgtgca gcattgcgga tcgccaactg caaactgttc | 1740 |
| cgcctgcagc ttcaacaggg gctctttaga ataagggtgc acagtccctg a | 1791 |

<210> SEQ ID NO 5
<211> LENGTH: 1791
<212> TYPE: DNA
<213> ORGANISM: Artificial Sequence
<220> FEATURE:
<223> OTHER INFORMATION: Synthetic Sequence

<400> SEQUENCE: 5

| | |
|---|---|
| atggctgaag gcagtgcagt ttccgatcct caacatgcgg ccagacttct ccgagcgctc | 60 |
| tctagctta gggaagagag cagattttgc gatgcacacc tggtcctcga cggggaagag | 120 |
| attcccgtgc aaaagaacat tctggccgct gccagcccat acattaggac caagctgaac | 180 |
| tataacccac cgaaagacga cgggtctaca tacaagatag agctggaagg gatctcagta | 240 |
| atggtgatgc gggagatact ggactatatc ttctctggtc agattcgcct caatgaggat | 300 |
| acgattcaag atgtagtcca ggccgctgat cttctgctgc tcactgatct caagaccctg | 360 |
| tgttgtgagt tcctcgaggg ctgcatcgcc gcagaaaact gcatcggtat tcgggatttc | 420 |
| gcgctgcact attgccttca ccacgtgcat tatctcgcca ccgaatatct tgagactcat | 480 |
| tttcgggatg taagctcaac agaagaattt cttgaactga gtcctcaaaa gttgaaggaa | 540 |
| gtcatctcat tggaaaagct caatgtcggc aatgagcgat acgtgttcga agcagtgatc | 600 |
| cggtggattg cccatgacac ggagattcgc aaagtgcaca tgaaagatgt gatgtctgca | 660 |
| ctttgggtta gtggcctgga cagctcctac ttgcgggagc agatgttgaa tgagcccctc | 720 |
| gtgcgggaaa tcgtgaaaga gtgtagtaac atcccgctct ctcaacctca gcagggagag | 780 |
| gcaatgctgg ctaactttaa gcctcggggc tactcagagt gcattgtcac tgtgggaggc | 840 |
| gaagagaggg tgagcagaaa gcccactgcc gccatgcgct gtatgtgccc cctgtacgac | 900 |
| cctaaccgcc agctgtggat agaactggcc cctctgtcta tgccaaggat aaaccatggt | 960 |
| gttctgagtg ccgagggctt tctcttcgtt ttcggcggac aggacgagaa caagcagacg | 1020 |

```
ctcagctccg gcgagaagta cgacccagat gctaacacat ggacggcgct gcccccctatg    1080 aatgaggctc gccataactt cgggattgta gagattgacg gaatgctgta cattctcgga    1140
ggagaggatg gagagaaaga acttatctca atggaatgtt acgacatcta ctccaagact    1200
tggactaaac agccagacct gacaatggtt aggaagatcg gatgctacgc agccatgaaa    1260
aagaaaatct atgccatggg cggaggatca tacggtaaac tgtttgagtc tgtcgaatgc    1320
tatgatccca gaacccagca gtggaccgcc atatgtccac tgaaagaacg gcgattcggg    1380
gctgtcgcat gcggtgtagc tatggagctg tatgttttg gcggcgtgag aagtagggag    1440
gacgctcaag gtcagaaat ggtgacatgc aaaagcgagt tctatcacga cgagtttaag    1500
cgatggatct atctgaatga ccagaattg tgtataccag catctagctc cttcgtgtat    1560
ggagcggtcc ctattggcgc tagcatctac gtcatcgggg atttggacac aggcaccaat    1620
tacgattatg tgagagagtt caaaaggagc actggcactt ggcatcacac caagccactc    1680
ctgccgtccg accttcgaag aacaggttgt gcagcattgc ggatcgccaa ctgcaaactg    1740
ttccgcctgc agcttcaaca ggggctcttt agaataaggg tgcacagtcc c              1791

<210> SEQ ID NO 6
<211> LENGTH: 1788
<212> TYPE: DNA
<213> ORGANISM: Artificial Sequence
<220> FEATURE:
<223> OTHER INFORMATION: Synthetic Sequence

<400> SEQUENCE: 6
gctgaaggca gtgcagtttc cgatcctcaa catgcggcca gacttctccg agcgctctct      60
agctttaggg aagagagcag attttgcgat gcacacctgg tcctcgacgg ggaagagatt     120
cccgtgcaaa agaacattct ggccgctgcc agcccataca ttaggaccaa gctgaactat     180
aacccaccga agacgacgg gtctacatac aagatagagc tggaagggat ctcagtaatg     240
gtgatgcggg agatactgga ctatatcttc tctggtcaga ttcgcctcaa tgaggatacg     300
attcaagatg tagtccaggc cgctgatctt ctgctgctca ctgatctcaa gaccctgtgt     360
tgtgagttcc tcgagggctg catcgccgca gaaaaactgca tcggtattcg ggatttcgcg     420
ctgcactatt gccttcacca cgtgcattat ctcgccaccg aatatcttga gactcatttt     480
cgggatgtaa gctcaacaga agaatttctt gaactgagtc ctcaaaagtt gaaggaagtc     540
atctcattgg aaaagctcaa tgtcggcaat gagcgatacg tgttcgaagc agtgatccgg     600
tggattgccc atgacacgga gattcgcaaa gtgcacatga agatgtgat gtctgcactt     660 tgggttagtg gcctggacag ctcctacttg cgggagcaga tgttgaatga gccctcgtg     720 cgggaaatcg tgaaagagtg tagtaacatc ccgctctctc aacctcagca gggagaggca     780
atgctggcta actttaagcc tcggggctac tcagagtgca ttgtcactgt gggaggcgaa     840
gagagggtga gcagaaagcc cactgccgcc atgcgctgta tgtgcccct gtacgacccct     900 aaccgccagc tgtggataga actggcccct ctgtctatgc aaggataaa ccatggtgtt     960 ctgagtgccg agggctttct cttcgttttc ggcggacagg acgagaacaa gcagacgctc    1020
agctccggcg agaagtacga cccagatgct aacacatgga cggcgctgcc cctatgaat    1080 gaggctcgcc ataacttcgg gattgtagag attgacggaa tgctgtacat tctcggagga    1140 gggatggag agaagaact tatctcaatg gaatgttacg acatctactc caagacttgg    1200
actaaacagc cagacctgac aatggttagg aagatcggat gctacgcagc catgaaaaag    1260
```

| | | | | |
|---|---|---|---|---|
| aaaatctatg | ccatgggcgg | aggatcatac | ggtaaactgt | ttgagtctgt cgaatgctat | 1320 |
| gatcccagaa | cccagcagtg | gaccgccata | tgtccactga | aagaacggcg attcggggct | 1380 |
| gtcgcatgcg | gtgtagctat | ggagctgtat | gttttttggcg | gcgtgagaag tagggaggac | 1440 |
| gctcaagggt | cagaaatggt | gacatgcaaa | agcgagttct | atcacgacga gtttaagcga | 1500 |
| tggatctatc | tgaatgacca | gaatttgtgt | ataccagcat | ctagctcctt cgtgtatgga | 1560 |
| gcggtcccta | ttggcgctag | catctacgtc | atcgggggatt | tggacacagg caccaattac | 1620 |
| gattatgtga | gagagttcaa | aaggagcact | ggcacttggc | atcacaccaa gccactcctg | 1680 |
| ccgtccgacc | ttcgaagaac | aggttgtgca | gcattgcgga | tcgccaactg caaactgttc | 1740 |
| cgcctgcagc | ttcaacaggg | gctctttaga | ataagggtgc | acagtccc | 1788 |

<210> SEQ ID NO 7
<211> LENGTH: 1794
<212> TYPE: DNA
<213> ORGANISM: Homo sapiens

<400> SEQUENCE: 7

| | | | | |
|---|---|---|---|---|
| atggctgagg | gcagtgccgt | gtctgaccct | cagcacgccg | cgcgtctgct gcgagcgctc | 60 |
| agctcttttcc | gcgaggagtc | tcgcttctgc | gacgcgcacc | tggtcctcga cggggaggag | 120 |
| atcccggtgc | agaagaacat | cctggcggcg | gccagcccgt | acatcaggac aaagttaaac | 180 |
| tataatcctc | caaagatga | tggatcaact | tataagattg | aacttgaagg gatatcggta | 240 |
| atggttatga | gagagatcct | ggattacatc | ttcagtgggc | agatcaggct aaatgaagat | 300 |
| acaatccaag | atgttgttca | ggcagctgac | ctgctgctac | tgacggacct taaaaccctg | 360 |
| tgctgtgagt | tttttggaagg | ctgcattgct | gctgagaact | gtattggtat ccgtgacttt | 420 |
| gcactacatt | actgcctcca | tcacgttcat | taccttgcca | cagaataccct ggagactcat | 480 |
| ttccgagacg | tcagcagcac | ggaagaattc | ttagagctga | gtcctcaaaa gcttaaagaa | 540 |
| gtgatttctc | ttgagaagtt | aaacgttggc | aatgaaagat | atgtctttga agcagtaatt | 600 |
| cgatggatag | cacatgatac | agaaataaga | aaggtccaca | tgaaggatgt tatgtcagct | 660 |
| ctgtggggttt | cagggttgga | ctccagttat | ttacgggaac | agatgctgaa tgaaccatta | 720 |
| gtacgagaaa | ttgtcaaaga | gtgtagcaat | ataccgctca | gccagccgca gcaaggggag | 780 |
| gcgatgctgg | ccaacttcaa | accccggggc | tactctgagt | gcatcgtgac tgttggtgga | 840 |
| gaagagagag | tttcacggaa | acccacagca | gcgatgcgat | gcatgtgccc tctctatgac | 900 |
| cctaacaggc | agctttggat | cgaactggcc | cctttaagca | tgccgagaat taaccatgga | 960 |
| gttctctcag | cagaaggatt | tttgtttgta | ttcgggggcc | aagatgaaaa taagcagact | 1020 |
| cttagctcag | gagaaaagta | tgatccagat | gcaaatacat | ggacagcatt gccacctatg | 1080 |
| aacgaggcaa | gacataactt | cggaattgtg | agatagatg | ggatgctgta cattttggga | 1140 |
| ggagaggatg | tgaaaagga | gctgattccc | atggagtgtt | acgatattta ttctaaaacc | 1200 |
| tggacaaagc | aacctgattt | gaccatggtc | agaaagatcg | gctgctatgc agctatgaaa | 1260 |
| aagaaaatct | acgccatggg | tggaggctcc | tacggaaagc | ttttttgagtc tgtagagtgt | 1320 |
| tatgatccca | ggacccagca | gtggactgcc | atatgtccac | taaaagagag gaggtttgga | 1380 |
| gcggtggcct | gtggagttgc | tatggagctg | tatgtgtttg | ggggagtccg aagtcgtgag | 1440 |
| gacgcccagg | gtagcgagat | ggtaacttgc | aagtccgagt | tctaccatga tgagtttaaa | 1500 |
| aggtggatct | atcttaacga | ccagaattta | tgcatccccg | ccagttcctc ttttgtttat | 1560 |
| ggagctgtac | ctataggagc | cagtatttat | gttattggag | atcttgatac aggtaccaat | 1620 |

| | |
|---|---:|
| tacgactacg tgcgtgagtt taaaagaagc acaggaacct ggcaccacac taaaccactc | 1680 |
| cttccatccg accttcgccg tacaggatgt gcagccttac gcattgcgaa ttgcaagctt | 1740 |
| ttccgcctgc agcttcagca aggcttattc cgtattcgtg ttcattcccc ttga | 1794 |

<210> SEQ ID NO 8
<211> LENGTH: 164
<212> TYPE: DNA
<213> ORGANISM: Artificial Sequence
<220> FEATURE:
<223> OTHER INFORMATION: Synthetic Sequence

<400> SEQUENCE: 8

| | |
|---|---:|
| gggcggagtt agggcggagc caatcagcgt gcgccgttcc gaaagttgcc ttttatggct | 60 |
| gggcggagaa tgggcggtga acgccgatga ttatataagg acgcgccggg tgtggcacag | 120 |
| ctagttccgt cgcagccggg atttgggtcg cggttcttgt ttgt | 164 |

<210> SEQ ID NO 9
<211> LENGTH: 48
<212> TYPE: DNA
<213> ORGANISM: Artificial Sequence
<220> FEATURE:
<223> OTHER INFORMATION: Synthetic Sequence

<400> SEQUENCE: 9

| | |
|---|---:|
| aataaagagc tcagatgcat cgatcagagt gtgttggttt tttgtgtg | 48 |

<210> SEQ ID NO 10
<211> LENGTH: 2029
<212> TYPE: DNA
<213> ORGANISM: Artificial Sequence
<220> FEATURE:
<223> OTHER INFORMATION: Synthetic Sequence

<400> SEQUENCE: 10

| | |
|---|---:|
| gggcggagtt agggcggagc caatcagcgt gcgccgttcc gaaagttgcc ttttatggct | 60 |
| gggcggagaa tgggcggtga acgccgatga ttatataagg acgcgccggg tgtggcacag | 120 |
| ctagttccgt cgcagccggg atttgggtcg cggttcttgt ttgttccgga aagccaccat | 180 |
| ggctgaaggc agtgcagttt ccgatcctca acatgcggcc agacttctcc gagcgctctc | 240 |
| tagctttagg gaagagagca gattttgcga tgcacacctg gtcctcgacg gggaagagat | 300 |
| tcccgtgcaa aagaacattc tggccgctgc cagcccatac attaggacca agctgaacta | 360 |
| taacccaccg aaagacgacg ggtctacata caagatagag ctggaaggga tctcagtaat | 420 |
| ggtgatgcgg gagatactgg actatatctt ctctggtcag attcgcctca atgaggatac | 480 |
| gattcaagat gtagtccagg ccgctgatct tctgctgctc actgatctca agaccctgtg | 540 |
| ttgtgagttc ctcgagggct gcatcgccgc agaaaactgc atcggtattc gggatttcgc | 600 |
| gctgcactat tgccttcacc acgtgcatta tctcgccacc gaatatcttg agactcattt | 660 |
| tcgggatgta agctcaacag aagaatttct tgaactgagt cctcaaaagt tgaaggaagt | 720 |
| catctcattg gaaaagctca atgtcggcaa tgagcgatac gtgttcgaag cagtgatccg | 780 |
| gtggattgcc catgacacgg agattcgcaa agtgcacatg aaagatgtga tgtctgcact | 840 |
| ttgggttagt ggcctggaca gctcctactt gcgggagcag atgttgaatg agcccctcgt | 900 |
| gcgggaaatc gtgaaagagt gtagtaacat cccgctctct caacctcagc agggagaggc | 960 |
| aatgctggct aactttaagc ctcggggcta ctcagagtgc attgtcactg tgggaggcga | 1020 |

| | |
|---|---|
| agagagggtg agcagaaagc ccactgccgc catgcgctgt atgtgccccc tgtacgaccc | 1080 |
| taaccgccag ctgtggatag aactggcccc tctgtctatg ccaaggataa accatggtgt | 1140 |
| tctgagtgcc gagggctttc tcttcgtttt cggcggacag gacgagaaca agcagacgct | 1200 |
| cagctccggc gagaagtacg acccagatgc taacacatgg acggcgctgc ccctatgaa | 1260 |
| tgaggctcgc cataacttcg ggattgtaga gattgacgga atgctgtaca ttctcggagg | 1320 |
| agaggatgga gagaaagaac ttatctcaat ggaatgttac gacatctact ccaagacttg | 1380 |
| gactaaacag ccagacctga caatggttag gaagatcgga tgctacgcag ccatgaaaaa | 1440 |
| gaaaatctat gccatgggcg gaggatcata cggtaaactg tttgagtctg tcgaatgcta | 1500 |
| tgatcccaga acccagcagt ggaccgccat atgtccactg aaagaacggc gattcggggc | 1560 |
| tgtcgcatgc ggtgtagcta tggagctgta tgtttttggc ggcgtgagaa gtagggagga | 1620 |
| cgctcaaggg tcagaaatgg tgacatgcaa aagcgagttc tatcacgacg agtttaagcg | 1680 |
| atggatctat ctgaatgacc agaatttgtg tataccagca tctagctcct tcgtgtatgg | 1740 |
| agcggtccct attggcgcta gcatctacgt catcggggat ttggacacag gcaccaatta | 1800 |
| cgattatgtg agagagttca aaaggagcac tggcacttgg catcacacca agccactcct | 1860 |
| gccgtccgac cttcgaagaa caggttgtgc agcattgcgg atcgccaact gcaaactgtt | 1920 |
| ccgcctgcag cttcaacagg ggctctttag aataagggtg cacagtccct gatgaaggcc | 1980 |
| taataaagag ctcagatgca tcgatcagag tgtgttggtt ttttgtgtg | 2029 |

<210> SEQ ID NO 11
<211> LENGTH: 2046
<212> TYPE: DNA
<213> ORGANISM: Artificial Sequence
<220> FEATURE:
<223> OTHER INFORMATION: Synthetic Sequence

<400> SEQUENCE: 11

| | |
|---|---|
| ggttcggtac cgggcggagt tagggcggag ccaatcagcg tgcgccgttc cgaaagttgc | 60 |
| cttttatggc tgggcggaga atgggcggtg aacgccgatg attatataag gacgcgccgg | 120 |
| gtgtggcaca gctagttccg tcgcagccgg gatttgggtc gcggttcttg tttgttccgg | 180 |
| aaagccacca tggctgaagg cagtgcagtt tccgatcctc aacatgcggc cagacttctc | 240 |
| cgagcgctct ctagctttag ggaagagagc agattttgcg atgcacacct ggtcctcgac | 300 |
| ggggaagaga ttcccgtgca aaagaacatt ctggccgctg ccagcccata cattaggacc | 360 |
| aagctgaact ataacccacc gaaagacgac gggtctacat acaagataga gctggaaggg | 420 |
| atctcagtaa tggtgatgcg ggagatactg gactatatct tctctggtca gattcgcctc | 480 |
| aatgaggata cgattcaaga tgtagtccag gccgctgatc ttctgctgct cactgatctc | 540 |
| aagaccctgt gttgtgagtt cctcgagggc tgcatcgccg cagaaaactg catcggtatt | 600 |
| cgggatttcg cgctgcacta ttgccttcac cacgtgcatt atctcgccac cgaatatctt | 660 |
| gagactcatt ttcgggatgt aagctcaaca gaagaatttc ttgaactgag tcctcaaaag | 720 |
| ttgaaggaag tcatctcatt ggaaaagctc aatgtcggca atgagcgata cgtgttcgaa | 780 |
| gcagtgatcc ggtggattgc ccatgacacg gagattcgaa agtgcacat gaaagatgtg | 840 |
| atgtctgcac tttgggttag tggcctggac agctcctact gcgggagca gatgttgaat | 900 |
| gagcccctcg tgcgggaaat cgtgaaagag tgtagtaaca tcccgctctc tcaacctcag | 960 |
| cagggagagg caatgctggc taactttaag cctcggggct actcagagtg cattgtcact | 1020 |
| gtgggaggcg aagagagggt gagcagaaag cccactgccg ccatgcgctg tatgtgcccc | 1080 |

```
ctgtacgacc ctaaccgcca gctgtggata gaactggccc ctctgtctat gccaaggata    1140
aaccatggtg ttctgagtgc cgagggcttt ctcttcgttt tcggcggaca ggacgagaac    1200
aagcagacgc tcagctccgg cgagaagtac gacccagatg ctaacacatg gacggcgctg    1260 cccctatga  atgaggctcg ccataacttc gggattgtag agattgacgg aatgctgtac    1320
attctcggag gagaggatgg agagaaagaa cttatctcaa tggaatgtta cgacatctac    1380
tccaagactt ggactaaaca gccagacctg acaatggtta ggaagatcgg atgctacgca    1440
gccatgaaaa agaaaatcta tgccatgggc ggaggatcat acggtaaact gtttgagtct    1500
gtcgaatgct atgatcccag aacccagcag tggaccgcca tatgtccact gaaagaacgg    1560
cgattcgggg ctgtcgcatg cggtgtagct atggagctgt atgttttttgg cggcgtgaga   1620 agtagggagg acgctcaagg gtcagaaatg gtgacatgca aaagcgagtt ctatcacgac    1680
gagtttaagc gatggatcta tctgaatgac cagaatttgt gtataccagc atctagctcc    1740
ttcgtgtatg gagcggtccc tattggcgct agcatctacg tcatcgggga tttggacaca    1800
ggcaccaatt acgattatgt gagagagttc aaaaggagca ctggcacttg gcatcacacc    1860
aagccactcc tgccgtccga ccttcgaaga acaggttgtg cagcattgcg gatcgccaac    1920
tgcaaactgt tccgcctgca gcttcaacag gggctcttta gaataagggt gcacagtccc    1980
tgatgaaggc ctaataaaga gctcagatgc atcgatcaga gtgtgttggt tttttgtgtg    2040
acgcgt                                                              2046
```